United States Patent
Andersen et al.

(10) Patent No.: US 7,132,400 B2
(45) Date of Patent: Nov. 7, 2006

(54) ALPHA-FETOPROTEIN PEPTIDES AND USES THEREOF

(75) Inventors: Thomas T. Andersen, Albany, NY (US); James A. Bennett, Delmar, NY (US); Herbert I. Jacobson, Albany, NY (US); Fassil B. Mesfin, Albany, NY (US)

(73) Assignee: CLF Medical Technology Acceleration Program, Inc., Clifton Park, NJ (US)

( * ) Notice: Subject to any disclaimer, the term of this patent is extended or adjusted under 35 U.S.C. 154(b) by 15 days.

(21) Appl. No.: 10/990,877

(22) Filed: Nov. 16, 2004

(65) Prior Publication Data

US 2005/0271587 A1 Dec. 8, 2005

Related U.S. Application Data

(62) Division of application No. 09/872,623, filed on Jun. 2, 2001, now Pat. No. 6,818,741.

(51) Int. Cl.
*A61K 38/00* (2006.01)

(52) U.S. Cl. ............................ 514/12; 514/13; 514/14; 514/15; 514/16

(58) Field of Classification Search ............ 514/12–16
See application file for complete search history.

(56) References Cited

U.S. PATENT DOCUMENTS

| | | | |
|---|---|---|---|
| 5,674,842 A | 10/1997 | Mizejewski | |
| 5,707,963 A | 1/1998 | Mizejewski | |
| 6,306,832 B1 | 10/2001 | Pietras | |

OTHER PUBLICATIONS

Gura Science vol. 273 p. 1041 (1997).*
Burgess et al, Journal of Cell Biology vol. 111 Nov. 1990 2129-2138.*
Lazar et al Molecular and Cellular Biology Mar. 1988 vol. 8 No. 3 1247-1252.*
Bennett, et al. (2001). Abstract Only "An α-fetoprotein-Derived Peptide Inhibits Estrogen Receptor Positive Breast Cancers, Sensitive and Resistant to Tamoxifen" *Proc. Amer. Assoc. Can. Res.* 42: 238.
Eisele, et al. (2001). *J. Pept. Res.* 57:29-38.
Eisele, et al. (2001). *J. Pept. Res.* 57:539-546.
Gekonge, et al. (2001). Abstract Only *Proc. Amer. Assoc. Can. Res.* 42: 239.
Jacobson, et al. (2000). Abstract from International Society for Preventive Oncology (ISPO) Meeting, Oct. 28-Oct. 31, 2000, http://www.cancerprev.org/Meetings/2000/Abstracts/Show?Num=556.
Mesfin, et al. (2000). *Biochim. Et. Biophys. Act.* 1501: 33-43.
Mesfin, et al. (2000).Abstract Only *Proc. Amer. Assoc. Can Res.* 41: 375.
Mesfin, et al. (2001). Abstract Only *Proc. Amer. Assoc. Can. Res* 42: 778.
Mesfin, et al. (2001). *J. Pept. Res.* 58: 246-256.
Mizejewski, et al. (1996). *Molec. Cell. Endo.* 118:15-23.
Vakharia, et al. (2000). Abstract Only. *Breast Can. Res. Treat.*63:41-52.
Duphinee, et al. (2000). Abstract Only. *Breast. Can. Res. Treat* 64:109.
MacColl, et al. (2001). Abstract Only. *Biochim. Biophys. ACTA Gen. Subj.* 1528(2-3): 127-134.
Li, et al. (2001). Abstract Only. *Clin. Chim. ACTA* 313:15-19.

* cited by examiner

*Primary Examiner*—Sheela J. Huff
(74) *Attorney, Agent, or Firm*—Ivor R. Elrifi, Esq.; Naomi S. Biswas, Esq.; Mintz Levin

(57) ABSTRACT

The subject invention addresses the need for methods of treatment and prevention of breast cancer, and other cancers, by providing a peptide of eight to twenty amino acids in length which comprises a hydrophilic analog of an alpha-fetoprotein peptide having SEQ ID NO:6: EMTPVNPG. The peptides may be linear, but are preferably cyclic. The peptides may be provided as dimers or other multimers. A composition comprising the peptide, an antibody that specifically binds to the peptide, a method of reducing estrogen-stimulated growth of cells using the peptide, as well as a method of treating or preventing cancer, such as breast cancer, are also provided. The treatment or prevention method can include the use of tamoxifen therapy in combination with the peptide therapy.

5 Claims, 19 Drawing Sheets

ALPHA-FETOPROTEIN PEPTIDES AND USES THEREOF

RELATED APPLICATIONS

This application is a divisional of U.S. patent application Ser. No. 09/872,623, filed Jun. 2, 2001, now U.S. Pat. No. 6,818,741.

The subject invention was made with support from National Institutes of Health Grant No. CA 87434 and U.S. Army Grant Nos. DAMD 17-99-1-9054 and DAMD 17-99-1-9370. The U.S. Government has certain rights in this invention.

FIELD OF THE INVENTION

The subject invention is directed generally to alpha-fetoprotein, and more particularly to peptides derived from alpha-fetoprotein and their use to treat and/or prevent cancers, including breast cancer.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Every year in the U.S., 180,000 new cases of breast cancer are diagnosed and approximately 60% of these are ER+ (Martin et al. 1994). Moreover, every year there are a substantial number of breast cancer recurrences and many of these are ER+. Tamoxifen has been the mainstay for medical treatment of ER+ breast cancer and has provided significant clinical benefit (Fisher et al. 1989; Fisher et al. 1998). However, there is a substantial number of ER+ breast cancers that are refractory to tamoxifen due to either intrinsic or acquired resistance. New treatments for these ER+, tamoxifen-refractory breast cancers are needed, and some promising agents are currently being evaluated in clinical trial. Letrozole, which blocks estrogen synthesis by inhibiting aromatase, and goserelin, which stifles ovarian release of estrogen by inhibiting gonadotropin release, are both being tested for this purpose (Goss et al. 2001; Nystedt et al. 2000).

Several population and epidemiologic studies as well as laboratory studies have indicated that alpha-fetoprotein (AFP) interferes with estrogen-dependent responses, including the growth-promoting effects of estrogen on breast cancer (Bennett et al. 1998). For example, Couinaud et al. (1973) have reported that women with AFP-secreting hepatomas develop amenorrhea which self-corrects following removal of the hepatoma, and Mizejewski et al. (1983) have shown that AFP inhibits the responsiveness of the uterus to estrogen. Jacobson et al. (1989) and Richardson et al. (1998) have shown that elevated levels of AFP during pregnancy are associated with subsequent reduction in lifetime risk for breast cancer, and Jacobson et al. have hypothesized that this could be caused by a diminution in estrogen-dependent breast cancers (Jacobson et al. 1989). Sonnenschein et al. (1980) have shown in rats that an AFP-secreting hepatoma prevents the growth of an estrogen-dependent breast cancer in the same rat. Finally, it has been shown that AFP purified from a human hepatoma culture and then injected into tumor-bearing immune-deficient mice stopped the growth of estrogen-receptor-positive (ER+), but not estrogen-receptor-negative (ER−), human breast cancer xenografts in these mice, and did so by a mechanism different from that of tamoxifen (Bennett et al. 1998).

More recently, the active site of AFP responsible for its antiestrotrophic activity has been identified (Mesfin et al. 2000). It consists of amino acids 472–479 (SEQ ID NO:6: EMTPVNPG), an 8-mer sequence in the 580-amino acid AFP molecule.

Aggregation of proteins and peptides has been seen with full length AFP as well as with subunits of AFP. Wu et al. (1985) showed that AFP tends to form aggregates, which may contribute to its loss of anti-estrotrophic activity during storage. Eisele et al. (2001) reported that oligomers of various sizes formed during storage of a 34-mer peptide (amino acids 447–480) derived from AFP. Similar aggregation behavior has been seen with a number of other protein and peptide pharmaceuticals including human interferon gamma (Kendrick et al. 1998), human calcitonin (Bauer et al. 1994), insulin (Sluzky et al. 1991), and synthetic beta-amyloid peptide (Hilbich et al. 1991; Christmanson et al. 1993; Halverson et al. 1990). Hughes et al. (1996) and Hilbich et al. (1992) reported inhibition of amyloid peptide aggregation by substitution of hydrophobic phenylalanine with hydrophilic threonine or by adding poly-lysine at the carboxy-terminus of the amyloid peptide.

As indicated above, tamoxifen is currently the most widely used agent for the treatment of estrogen-responsive breast cancers and has provided significant benefit to women with this disease (Fisher et al. 1989; Fisher et al. 1998). However, one problem connected with its clinical use is that not all ER+ breast cancers are sensitive to this drug. About one-third to one-sixth (depending on the lab cutoff for ER positivity) of the ER+, newly diagnosed breast cancers do not respond to tamoxifen (Jensen et al. 1996). Moreover, it is not uncommon that women whose disease is being successfully managed by tamoxifen therapy will in time experience recurrence during treatment apparently because their tumor has acquired resistance to the drug. Because these two groups constitute a substantial number of woman whose disease fails to respond to tamoxifen therapy, it is important to seek alternative treatment methods.

SUMMARY OF THE INVENTION

The subject invention addresses the need for methods of treatment and prevention of breast cancer, and other cancers, by providing a peptide of eight to twenty amino acids in length which comprises a hydrophilic analog of an alpha-fetoprotein peptide having SEQ ID NO:6: EMTPVNPG. The peptides may be linear, but are preferably cyclic. The peptides may be provided as dimers or other multimers. A composition comprising the peptide, an antibody that specifically binds to the peptide, a method of reducing estrogen-stimulated growth of cells using the peptide, as well as a method of treating or preventing cancer, such as breast cancer, are also provided. The treatment or prevention method can include the use of tamoxifen therapy in combination with the peptide therapy.

BRIEF DESCRIPTION OF THE DRAWINGS

These and other features and advantages of this invention will be evident from the following detailed description of preferred embodiments when read in conjunction with the accompanying drawings in which:

(FIG. 1a) Peptide dose-response. (FIG. 1b) Anti-estrotrophic activity as a function of peptide storage time at −20° C. in the lyophilized state, 1 µg peptide per mouse;

(FIG. 3a) dose-response. (FIG. 3b) effect of time in storage;

(FIG. 4a) dose-response. (FIG. 4b) effect of time in storage;

(FIG. 6a) dose-response. (FIG. 6b) effect of time in storage;

(FIG. 9a) MCF-7 tumors. At day 30 after tumor implantation, tumor volumes in the $E_2$+Pep group and in the $E_2$+Tam group were significantly different from tumor volumes in the $E_2$ alone group, $p<0.05$, Wilcoxon Ranks Sum Test. (FIG. 9b) MCF-7 subline made resistant to tamoxifen in culture. At day 30 after tumor implantation, tumor volumes in the $E_2$+Pep group but not in the $E_2$+Tam group were significantly different from tumor volumes in the $E_2$ alone group, $p<0.05$, Wilcoxon Ranks Sum Test;

DETAILED DESCRIPTION OF THE INVENTION

Figure 1A:
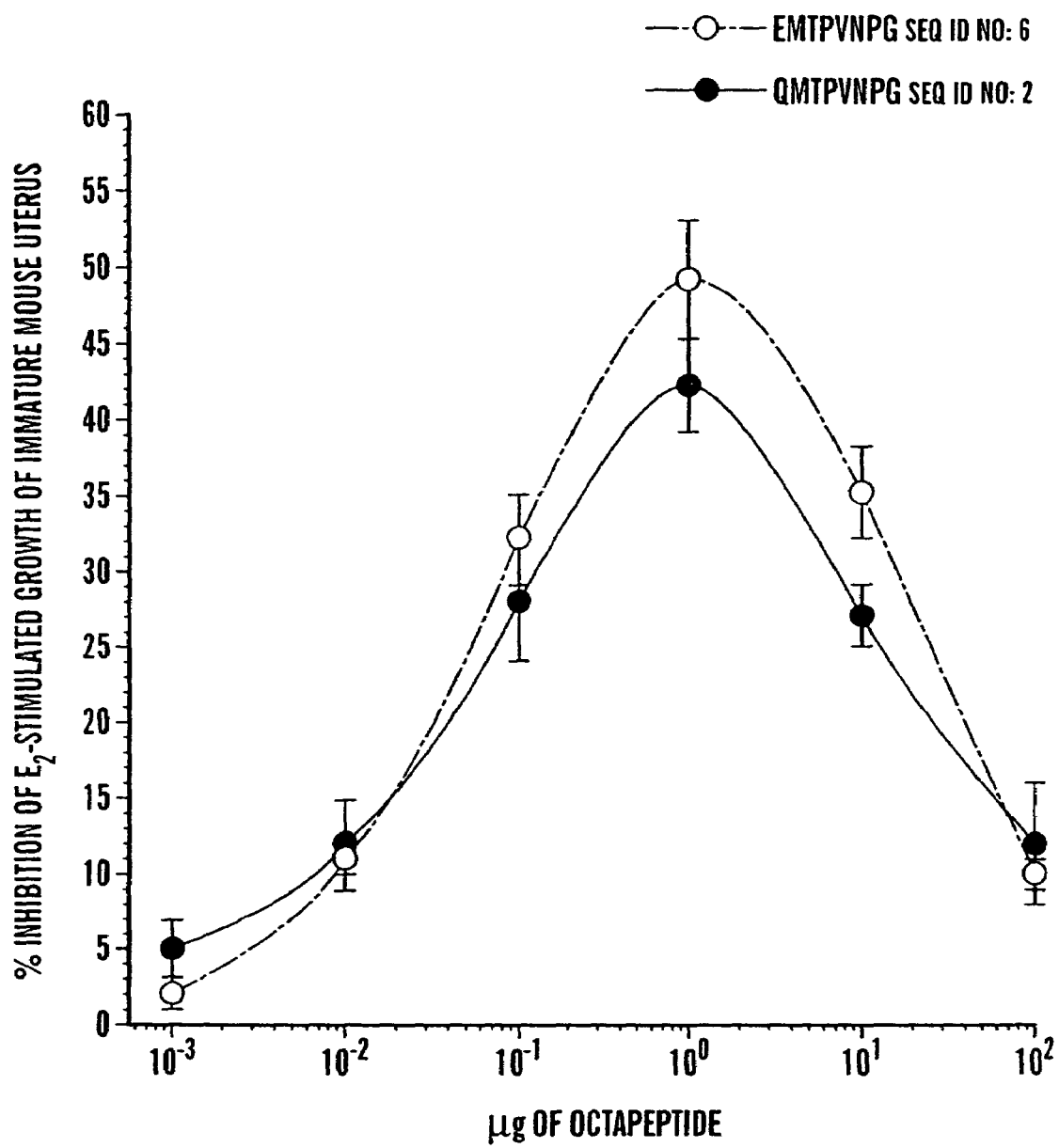
FIGS. 1a and 1b illustrate the anti-uterotrophic activity of octapeptide, SEQ ID NO:2: QMTPVNPG, measured in the immature mouse uterine growth assay. Peptide or vehicle control was injected i.p. into immature female Swiss mice. One hour later 0.5 µg of $E_2$ or vehicle control was injected i.p. into these mice. Twenty-two hours later, uteri were dissected and weighed. Percent inhibition of $E_2$-stimulated growth of uterus by peptide was calculated as described in Materials and Methods. There were five to eight replicate mice per treatment group.

The subject invention provides a peptide of eight to twenty amino acids in length which comprises a hydrophilic analog of an alpha-fetoprotein peptide having SEQ ID NO:6: EMTPVNPG. The peptide may be linear or cyclic, and may include (D) as well as (L) amino acids. For imaging purposes, the peptide may be labeled with a detectable marker, such as a radiolabel. The radiolabel may be provided by attaching an additional amino acid to the peptide, the additional amino acid being radiolabeled. In one embodiment, the peptide comprises an amino acid sequence selected from the group consisting of:

```
SEQ ID NO:2:  QMTPVNPG

SEQ ID NO:3:  QMTPVNPGE

SEQ ID NO:4:  EMTOVNOG

SEQ ID NO:5:  EMTOVNOGQ

SEQ ID NO:7:  EMTPVNPGQ

SEQ ID NO:8:  EMTOVNPG

SEQ ID NO:9:  EMTOVNPGQ

SEQ ID NO:10: EMTPVNOG
and

SEQ ID NO:11: EMTPVNOGQ,
``` or a peptidomimetic of said peptide.

Dimers of the said peptides (such as a peptide having SEQ ID NO:4 in combination with a peptide having SEQ ID NO:5, or a peptide having SEQ ID NO:3 in combination with a peptide having SEQ ID NO:10), or other multimers (three or more peptides), are also provided by the subject invention.

The peptide is preferably provided as a composition which comprises the peptide and a suitable carrier. In order to improve stability and shelf-life, in one embodiment the peptide is provided as a composition with a stabilization excipient (such as dodecyl maltoside or mannitol).

Antibodies to the peptide are also provided, which are useful to track the peptides in the body. The peptides can also be tracked by directly labeling the peptides themselves with a detectable marker such as a radiolabel, as discussed above.

The peptides of the subject invention are useful in a method of reducing estrogen-stimulated growth of cells. This is accomplished by exposing the cells to the peptide, which can occur in vitro and in vivo. Since tamoxifen (and similar substances) have been used previously in the treatment of breast cancer, the subject invention also provides a method of reducing estrogen-stimulated growth of cells which further comprises exposing the cells to tamoxifen (used in it's broadest interpretation to include analogs and derivatives thereof) before, during, or after exposing the cells to the peptide.

Further provided is a method of treating or preventing cancer in a subject, which comprises administering to the subject an amount of the peptide sufficient to treat or prevent cancer. Such cancers include, for example, estrogen-dependent cancers such as breast cancer. As stated above, this peptide therapy can be combined with administration of tamoxifen to enhance treatment and/or prevention.

The peptides of the subject invention have been designed as therapeutic agents that are effective against breast cancer. They also have use in the fight against prostate cancer and other cancers which are affected by the steroid hormone/thyroid hormone superfamily of receptors. It may be that these peptides or analogs would serve as first-line defense agents, but it is also possible that they would serve as adjunct therapeutic agents. For example, the currently utilized drug-of-choice in the fight against breast cancer is tamoxifen, but tamoxifen suffers from a side effect of causing uterine cancer in 0.2% of users. The peptides described in this invention inhibit the uterine growth that is stimulated by tamoxifen, and so may be useful as adjunct therapy along with tamoxifen.

Other endocrine-related situations in which these peptides might be active include those where AFP has been shown to improve symptoms, such as inflammatory diseases such as rheumatoid arthritis. AFP has also been shown to play a therapeutic role in myasthenia gravis and an AFP analog may be useful in this situation. AFP has been reported to play a role in maternal tolerance of the fetus and therefore an active analog of AFP should have use in organ transplant rejection. Also, use against lymphoproliferative disorders would be appropriate. Since AFP and AFP analogs dampen the response to estrogen and, in all likelihood, progesterone, an AFP analog may be useful in situations such as birth control, abortion, endometriosis, and menopause. For example, post-menopausal estrogen supplementation for bone effects might be a situation in which adjunct treatment with these peptides may prove effective.

These peptides, which are derivatives of a safe, naturally-occurring protein (AFP), are likely to be significantly less toxic than tamoxifen or raloxifene. These analogs may thus be useful as preventive agents so that breast (or prostate or other) cancers do not occur.

By modifying these agents with radiolabel or other identifiable means, it is likely that they would serve as agents that could detect breast (or other) cancers earlier than can any other existing method.

The preferred route of administration of peptides is currently injection, which may be acceptable for treatment of cancer or for early detection of cancer. For prevention, transdermal administration of peptides may be preferable, so that administration by means of a patch that may be worn while delivering a prescribed dose of drug should be considered.

Antibodies to the peptides have commercial value for use in measuring the concentration of drug in serum, and for other reasons. Similarly, radiolabeled (or otherwise labeled) peptides and peptidomimetics can be used for detecting such agents in serum or for investigational purposes such as exploring the mechanism of action of these agents.

In the context of this invention, to "expose" cells (including the cells of tissues) to a peptide means to add the peptide, usually in a liquid carrier, to a cell suspension or tissue sample in vitro, or to administer the peptide to cells or tissues within an animal (including a human) subject in vivo.

For therapeutics, the formulation of therapeutic compositions and their subsequent administration is believed to be within the skill in the art. In general, for therapeutics, a patient suspected of needing such therapy is given a peptide in accordance with the invention, commonly in a pharmaceutically acceptable carrier, in amounts and for periods which will vary depending upon the nature of the particular disease, its severity and the patient's overall condition. The pharmaceutical compositions may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable. The peptides may be provided in the form of liposome delivery vehicles.

Compositions for parenteral, intrathecal or intraventricular administration may include sterile aqueous solutions which may also contain buffers, diluents and other suitable additives.

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual peptides, and can generally be calculated based on $IC_{50}$'s or $EC_{50}$'s. For example, given the molecular weight of a peptide and an effective dose such as an $IC_{50}$, for example (derived experimentally), a dose in mg/kg is routinely calculated.

The peptide drugs, and peptidomimetics thereof (including mimotopes and anti-mimotopes) can be made using various methods known in the art. A monoclonal antibody can be prepared which specifically binds to the peptide, thereby interfering with activity.

The monoclonal antibodies can be produced by hybridomas. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell, A. M., "Monoclonal Antibody Technology: Laboratory Techniques in Biochemistry and Molecular Biology", Elsevier Science Publishers, Amsterdam, The Netherlands (1984); St. Groth, et al., J Immunol Methods 35:1–21 (1980)). Any animal (mouse, rabbit, etc.) which is known to produce antibodies can be immunized with the peptide (or an antigenic fragment thereof). Methods for immunization are well known in the art. Such methods include subcutaneous or intraperitoneal injection of the peptide. One skilled in the art will recognize that the amount of the peptide used for immunization will vary based on the animal which is immunized, the antigenicity of the peptide, and the site of injection.

The peptide which is used as an immunogen may be modified or administered in an adjuvant in order to increase the peptide's antigenicity. Methods of increasing the antigenicity of a peptide are well known in the art and include, but are not limited to, coupling the antigen with a heterologous protein (such as a globulin or beta-galactosidase) or through the inclusion of an adjuvant during immunization.

For monoclonal antibodies, spleen cells from the immunized animals are removed, fused with myeloma cells, such as SP2/O—Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz, et al., Exp Cell Res 175:109–124 (1988)).

Hybridomas secreting the desired antibodies are cloned and the class and subclass are determined using procedures known in the art (Campbell, A. M., "Monoclonal Antibody Technology: Laboratory Techniques in Biochemistry and Molecular Biology", Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Once a monoclonal antibody which specifically binds to the peptide is identified, the monoclonal can be used to identify peptides capable of mimicking the inhibitory activity of the monoclonal antibody. One such method utilizes the development of epitope libraries and biopanning of bacteriophage libraries. Briefly, attempts to define the binding sites for various monoclonal antibodies have led to the development of epitope libraries. Parmley and Smith developed a bacteriophage expression vector that could display foreign epitopes on its surface (Parmley, S. F. & Smith, G. P., Gene 73:305–318 (1988)). This vector could be used to construct large collections of bacteriophage which could include virtually all possible sequences of a short (e.g. six-amino-acid) peptide. They also developed biopanning, which is a method for affinity-purifying phage displaying foreign epitopes using a specific antibody (see Parmley, S. F. & Smith, G. P., Gene 73:305–318 (1988); Cwirla, S. E., et al., Proc Natl Acad Sci USA 87:6378–6382 (1990); Scott, J. K. & Smith, G. P., Science 249:386–390 (1990); Christian, R. B., et al., J Mol Biol 227:711–718 (1992); Smith, G. P. & Scott, J. K., Methods in Enzymology 217:228–257 (1993)).

After the development of epitope libraries, Smith et al. then suggested that it should be possible to use the bacteriophage expression vector and biopanning technique of Parmley and Smith to identify epitopes from all possible sequences of a given length. This led to the idea of identifying peptide ligands for antibodies by biopanning epitope libraries, which could then be used in vaccine design, epitope mapping, the identification of genes, and many other applications (Parmley, S. F. & Smith, G. P., Gene 73:305–318 (1988); Scott, J. K., Trends in Biochem Sci 17:241–245 (1992)).

Using epitope libraries and biopanning, researchers searching for epitope sequences found instead peptide sequences which mimicked the epitope, i.e., sequences which did not identify a continuous linear native sequence or necessarily occur at all within a natural protein sequence. These mimicking peptides are called mimotopes. In this manner, mimotopes of various binding sites/proteins have been found.

The sequences of these mimotopes, by definition, do not identify a continuous linear native sequence or necessarily occur in any way in a naturally-occurring molecule, i.e. a naturally occurring protein. The sequences of the mimotopes merely form a peptide which functionally mimics a binding site on a naturally-occurring protein.

Many of these mimotopes are short peptides. The availability of short peptides which can be readily synthesized in large amounts and which can mimic naturally-occurring sequences (i.e. binding sites) offers great potential application.

Using this technique, mimotopes to a monoclonal antibody that recognizes the peptide of the subject invention can be identified. Once the sequence of the mimotope is determined, the peptide drugs can be chemically synthesized.

The peptides for use in the subject invention can contain any naturally-occurring or non-naturally-occurring amino acids, including the D-form of the amino acids, amino acid derivatives and amino acid mimics, so long as the desired function and activity of the peptide is maintained. The choice of including an (L)- or a (D)-amino acid in the peptide depends, in part, on the desired characteristics of the peptide. For example, the incorporation of one or more (D)-amino acids can confer increased stability on a peptide and can allow a peptide to remain active in the body for an extended period of time. The incorporation of one or more (D)-amino acids can also increase or decrease the pharmacological activity of a peptide.

The peptide may also be cyclized, since cyclization may provide the peptide with superior properties over their linear counterparts. Cyclization is discussed further below.

Modifications to the peptide backbone and peptide bonds thereof are encompassed within the scope of amino acid mimic or mimetic (the resulting peptide being a peptidomimetic). Such modifications can be made to the amino acid, derivative thereof, non-amino acid moiety or the peptide either before or after the amino acid, derivative thereof or non-amino acid moiety is incorporated into the peptide. What is critical is that such modifications mimic the peptide backbone and bonds which make up the same and have substantially the same spacial arrangement and distance as is typical for traditional peptide bonds and backbones. An example of one such modification is the reduction of the carbonyl(s) of the amide peptide backbone to an amine. A number of reagents are available and well known for the reduction of amides to amines such as those disclosed in Wann et al., JOC 46:257 (1981) and Raucher et al., Tetrahedron Lett 21:14061 (1980). An amino acid mimic is, therefore, an organic molecule that retains the similar amino acid pharmacophore groups as are present in the corresponding amino acid and which exhibits substantially the same spatial arrangement between functional groups.

The substitution of amino acids by non-naturally occurring amino acids and amino acid mimics as described above can enhance the overall activity or properties of an individual peptide thereof based on the modifications to the backbone or side chain functionalities. For example, these types of alterations can enhance the peptide's stability to enzymatic breakdown and increase biological activity. Modifications to the peptide backbone similarly can add stability and enhance activity.

One skilled in the art, using the identified sequences can easily synthesize the peptides for use in the invention. Standard procedures for preparing synthetic peptides are well known in the art. The novel peptides can be synthesized using: the solid phase peptide synthesis (SPPS) method of Merrifield, J Am Chem Soc 85:2149 (1964) or modifications of SPPS; or, the peptides can be synthesized using standard solution methods well known in the art (see, for example, Bodanzsky, "Principles of Peptide Synthesis", 2d Ed., Springer-Verlag (1993)). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, Proc Natl Acad Sci USA 82:5131 (1985).

Materials and Methods

Cell Lines. T47D and MDA-MB-231 human breast cancer cell lines were purchased from the American Type Culture Collection (Manassas, Va.). Growth medium for T47D cells consisted of RPMI 1640 (Life Technologies, Germantown, Md.) supplemented with 10% fetal bovine serum (Life Technologies) and 8 µg/ml bovine insulin (Sigma, St. Louis, Mo.). Growth medium for MDA-MB-231 consisted of Dulbecco's Modified Eagle Medium (Life Technologies) supplemented with L-glutamine (2 mM), non-essential amino acids (1%, Life Technologies) and bovine insulin (1 µg/ml). The MCF-7 cell line was obtained from Dr. Alberto C. Baldi, Institute of Experimental Biology and Medicine, Buenos Aires, Argentina, and was maintained as previously described by Gierthy et al. (1991). This strain of MCF-7 demonstrated 17β-estradiol ($E_2$) sensitivity in regard to induction of tissue plasminogen activator, cell proliferation and in vivo tumor growth and was sensitive to the suppression of these effects by tamoxifen (12-Continuous exposure of these cells to 1 µM tamoxifen citrate during routine culture conditions (1:10 subculture ratio once a week) resulted after 6 months in a strain that was resistant to the suppressive effects of tamoxifen in vitro.

Peptide Synthesis. Peptides were synthesized using FMOC solid phase peptide synthesis on a Pioneer Peptide Synthesis System (PerSeptive Biosystem, Inc., Framingham, Mass.)(see also Mesfin et al. 2000). Briefly, peptides were assembled on a solid support (Fmoc-Polyethylene-Graft Polystyrene Support) from the C-terminus, reacting the deblocked amino (N)-terminus of support-bound amino acid with the activated carboxyl (C)-terminus of the incoming amino acid to form an amide bond. Amino acids used in the synthesis had their $N^\alpha$-amino group protected by the 9-fluorenylmethoxycarbonyl (Fmoc) group, which was removed by piperidine at the end of each cycle in the synthesis. Side-chain protecting groups of amino acids were Asn(Trt), Gln(Trt), Glu(OtBu), Hyp(tBu), Thr(tBu) which were deprotected by trifluoroacetic acid (TFA) after peptide synthesis. The carboxyl-group of the amino acid was activated with HATU [O-(7-azabenzotriazol-1-yl)-1,1,3,3-tetramethyluronium hexafluorophosphate] obtained from PerSeptive Biosystems Inc. The specific amino acid derivatives, supports, and reagents used in the synthesis were purchased from PerSeptive Biosystems Inc. and NovaBiochem, San Diego, Calif.

After synthesis was completed, the resin was washed three times with 100% propanol and the cleavage reaction was achieved by incubating the resin in 10 ml trifluoroacetic acid/thioanisole/anisole/1,2-ethanedithiol (90:5:2:3) per 0.5 g resin for 5 hours. The cleavage reaction mixture was filtered using a sintered glass funnel to separate the solid resin from the peptide solution. Filtrate volume was reduced to 1 ml by evaporation facilitated with a gentle stream of air and the peptides were precipitated by addition of 15 ml dry-ice chilled ethyl ether. The peptides were allowed to settle for five minutes at −80° C., and the supernatant was aspirated. The peptides were then washed twice in similar manner with 15 ml of ethyl ether. After three further washings with 15 ml of ethyl acetate:diethylether (1.5:1, room temperature), the peptides were dissolved in deionized water, purified by reverse phase HPLC (see details below), lyophilized, and stored at −20° C.

Cyclization of the Peptides. Cyclization of peptides was accomplished using methods described by Kates et al. (17, 18). Briefly, N-alpha FMOC-L-glutamic acid-alpha-allyl ester at the C-terminus of the synthetic peptide was coupled to the resin via the gamma carboxylic acid. Removal of the $N^\alpha$-FMOC allowed the remaining amino acids to be incorporated sequentially into the growing peptide. A free alpha-carboxyl group was then generated upon removal of the allyl group from the C-terminal Glu (18). This alpha-carboxyl group was then coupled to the free N-terminal residue of the peptide (while on the resin) in order to generate the cyclic peptide, which was then removed from the resin in such a way as to yield the gamma-carboxamido derivative (i.e, Q). The cyclic peptide was then purified and characterized as described below.

Purification of Peptides. Purification of peptides was accomplished using a Waters Delta-Pak $C_{18}$ (19 mm×30 cm) reverse phase column with a pore diameter of 300 Å on a Waters 650E liquid chromatography system equipped with a 486 adjustable absorbance detector and a 600E controller. The column was operated with gradient using a 0.1% trifluoroacetic acid in water as solvent A and 0.1% trifluoroacetic acid in acetonitrile as solvent B. The gradient was set as follows: 100% solvent A for the first 4 min, followed by increasing acetonitrile from 0–40% solvent B over the next 35 min then isocratically at 40% B for 11 min, and followed by a linear gradient of 40–100% B over 10 min all with a flow rate of 7 ml/min. Peptide was monitored at 230 nm and fractions containing pure peptide (>95% purity) were pooled together and lyophilized.

Peptide Characterization. Amino acid analyses of all peptides were performed using the Waters AccQ-Tag amino acid analysis system (19;20). Peptides were analyzed by mass spectrometry using standard alpha-cyano-4-hydroxysinnipinic acid and sinnipinic acid matrices. Integrity of cyclized peptides was further validated using the Kaiser test (21) to ensure absence of free terminal amino group.

Immature Mouse Uterine Growth Assay. A bioassay for anti-estrotrophic activity was performed using an immature mouse uterine growth assay (22). Swiss/Webster female mice, 6–8 g in body weight (13–15 days old), were obtained from Taconic Farms (Germantown, N.Y.). Mice were weighed and distributed into treatment groups (typically 5 mice per group) such that each group contained the same range of body weight. In a typical experiment, each group received two sequential intraperitoneal injections spaced one hour apart. Test material or vehicle control for that material was contained in the first injectant. Estradiol ($E_2$) or vehicle control for $E_2$ was contained in the second injectant. Twenty-two hours after the second injection, uteri were dissected, trimmed free of mesenteries, and immediately weighed. The uterine weights were normalized to mouse body weights (mg uterine weight/g of body weight) to compensate for differences in body weight among litters of the same age. Experiments employed a minimum of five mice per group, and the mean normalized uterine weight±standard error for each group was calculated. Percent growth inhibition in a test group was calculated from the normalized uterine wet weights as described below.

$$\text{Growth Inhibition (\%)} = \frac{\text{Full } E_2\text{-Stimulation} - E_2\text{-Stimulation in Test Group}}{\text{Full } E_2\text{-Stimulation} - \text{No } E_2\text{-Stimulation}} \times 100\%$$

Differences between groups were evaluated, employing the non-parametric Wilcoxon Sum of Ranks test (one-sided). In all cases, growth inhibitions that were greater than 25% were significant at $p \leq 0.05$.

Human Breast Cancer Xenograft Assay. A bioassay for anti-breast cancer activity was performed according to Bennett et al. (23;24). Confluent MCF-7 human breast cancer cells were trypsinized into suspension and pelleted by centrifugation at 200× g. The pellet was then solidified into a fibrin clot by exposing it to 10 µl of fibrinogen (50 mg/ml) and 10 µl of thrombin (50 units/ml). The solid mass of MCF-7 cells was then cut into pieces 1.5 mm in diameter. A tumor segment of ~1.5 mm in diameter was implanted under the kidney capsule of an immunodeficient ICR-SCID male mouse (Taconic Farms) that weighed about 25 g. Estrogen supplementation was accomplished by s.c. implantation of a silastic tubing capsule containing solid $E_2$ inserted on the day of tumor implantation. Peptide was injected i.p. every twelve hours at a dose of 1 µg per mouse. Tumor growth was monitored during survival laparotomy at 10-day intervals by measurement of the diameters of the short (d) and long axes (D) of each tumor, using a dissecting microscope equipped with an ocular micrometer. Tumor volumes were calculated using the formula $(n/6)(d)^2 D$, assuming the tumor shape to be an ellipsoid of revolution around its long axis (D). There were five to seven replicate mice included in each treatment group. Mean tumor volume±standard error in each group was calculated for display of growth curves. Significance of differences between groups were tested using the one-sided Wilcoxon Sum of Ranks Test.

Assessment of Estrogen Receptor Antagonism. Commercially obtained rabbit uteri (Pel-Freez Biological, Rogers, Ark.) were used as a source of estrogen receptor. Uteri were pulverized in a stainless steel impact mortar under liquid nitrogen and homogenized (20% w/v) in assay buffer [10 mM Tris (pH 7.4), 1.5 mM EDTA, 10% glycerol, 10 mM monothioglycerol, and 10 mM sodium molybdate] on ice. Centrifugation (50,000× g) for 1 h yielded a supernatant containing cytosol, which was adjusted with assay buffer to 2.5 mg protein/ml. All incubations were carried out in triplicate, each containing 100 µl of cytosol, 20 µl of 10 mM 6,7-[$^3$H]estradiol (50 Ci/mmol; DuPont Pharmaceuticals Company, Wilmington, Del., U.S.A. ), and 80 µl of putative antagonist in assay buffer. Total count tubes received 20 µl of [$^3$H]estradiol and 180 µl of assay buffer. After incubation overnight at 4° C., all but the total count tubes received 300 µl of dextran-coated charcoal suspension; tubes were agitated for 15 min and then centrifuged (1,000× g) for 15 min. Supernatants were decanted into counting vials, scintillant was added, and protein-bound tritium was determined by liquid scintillation counting.

EXAMPLE I

Development of a Synthetic Cyclized Peptide Derived from Alpha-Fetoprotein.

Figure 1B:
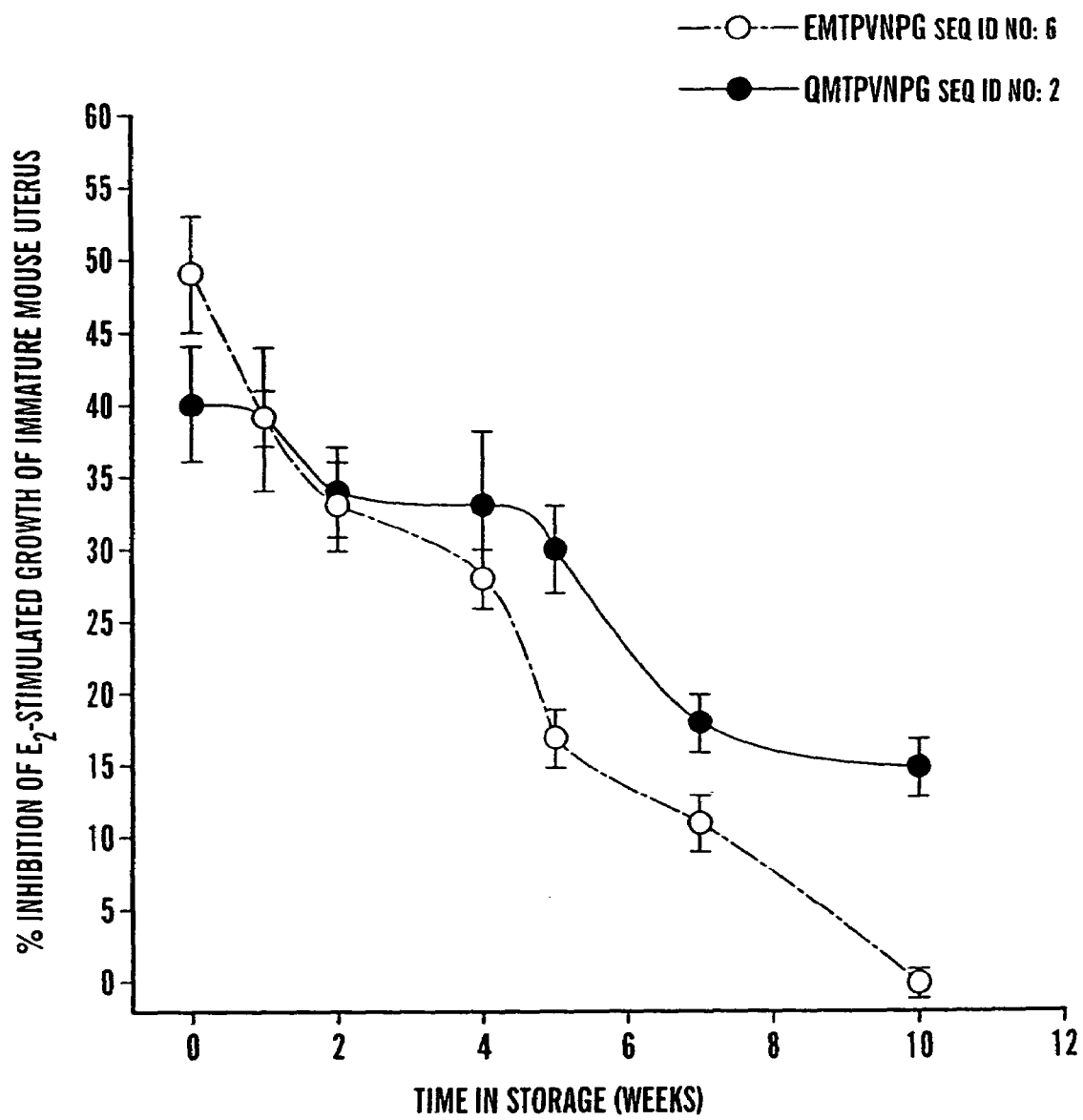

Earlier, it had been shown that an energy-minimized structure of octapeptide SEQ ID NO:6: EMTPVNPG indicated that the peptide had potential to form a horseshoe shaped structure (Mesfin et al. 2000). Energy-minimization studies of an analog of this peptide, that would be generated by substitution of the N-terminal glutamic acid with glutamine (SEQ ID NO:2: QMTPVNPG), indicated that this product would have potential to bow even further inward and form a pseudo-cyclic structure. This pseudo-cyclic structure may have greater structural stability due to hydrogen bonding between the N-terminal glutamine gamma-carboxamide group and the C-terminal glycine alpha-carboxamide. This linear analog (SEQ ID NO:2: QMTPVNPG) was therefore synthesized, and its biological activity was compared to SEQ ID NO:6: EMTPVNPG in the estrogen-dependent immature mouse uterine growth assay. SEQ ID NO:2: QMTPVNPG inhibited the estrogen-stimulated growth of mouse uterus with an optimal dose of 1 µg/mouse (FIG. 1*a*), similar to the native octapeptide SEQ ID NO:6: EMTPVNPG. These results suggested that the substitution of glutamic acid to glutamine did not detract from the biological activity and also did not change the biphasic nature of the dose-response curve. Shelf-life studies indicated that SEQ ID NO:2: QMTPVNPG stored somewhat better than the native octapeptide (SEQ ID NO:6: EMTPVNPG), but its anti-estrotrophic activity also diminished to insignificant levels after five weeks of storage (FIG. 1b), indicating that the putative stabilization was not sufficient to prevent loss of biological activity during storage.

As shown in Table I, aged octapeptide SEQ ID NO:2: QMTPVNPG, stored in the lyophilized state at −20° C. for over one year, was completely biologically inactive. However, brief treatment with 4 M urea restored its biological activity, suggesting that this peptide might have aggregated during storage, resulting in loss of biological activity. A scrambled form of the Q octapeptide had no biological activity either with or without urea treatment. The biological activity of stored inactive SEQ ID NO:6: EMTPVNPG was likewise regenerated by 4 M urea.

Figure 2A:
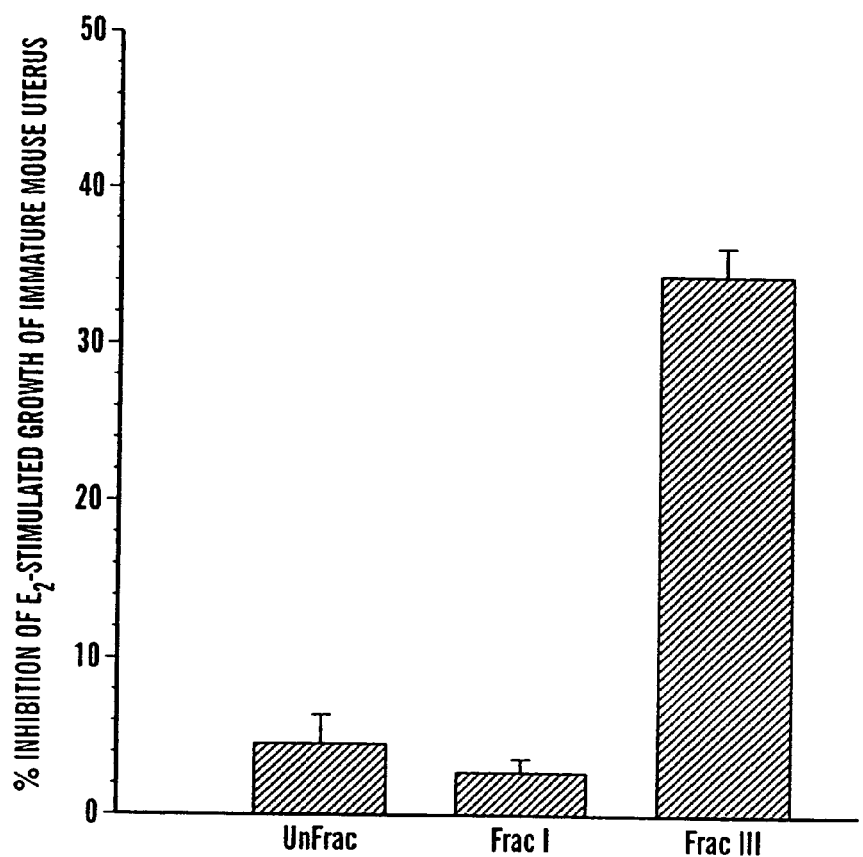
FIGS. 2a and 2b illustrate the anti-uterotrophic activity of fractions from gel-filtration chromatography of stored octapeptide, SEQ ID NO:2: QMTPVNPG. Peptide, SEQ ID NO:2: QMTPVNPG, was fractionated using a Waters SW 200 gel-filtration column using phosphate buffered saline pH 7.4 as mobil phase. Fractions which had significant UV absorbance at 230 nm were collected at twenty second intervals. The first fraction (Frac I), the last fraction (Frac III), and the starting material (UnFrac) were all tested in the immature mouse uterine growth assay as described in FIGS. 1a and 1b. One µg of peptide was injected i.p. into mice in all cases, and percent inhibiton of $E_2$-stimulated growth was measured.
Figure 2B:
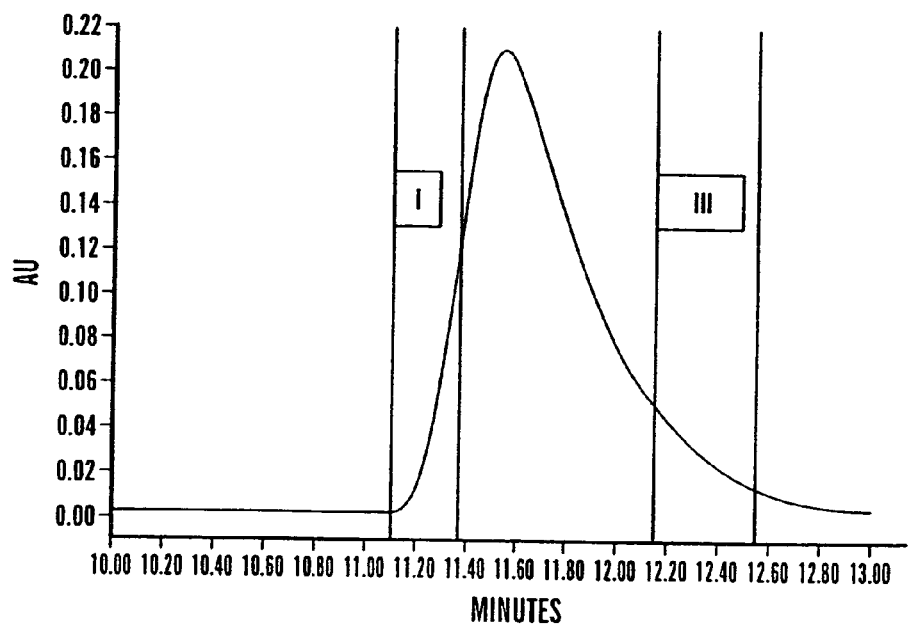

Gel-filtration column chromatography of aged peptide (SEQ ID NO:2: QMTPVNPG) yielded a single peak (FIG. 2b) which became broader as a function of time in storage. This suggested that small aggregates (dimers, trimers) were forming during storage. Although gel filtration chromatography has low resolution for monomers, dimers, and trimers in this size range (841 Da to 2523 Da), the width of the peak suggested that aggregates might be separating from monomer. Fractions from different portions of the broad peak from aged, chromatographed peptide were therefore tested for biological activity. The higher molecular weight fraction (FIG. 2b, left side of peak) was biologically inactive while the lower molecular weight fraction (FIG. 2b, right side of peak) was active in the estrogen-dependent immature mouse uterine growth assay. This suggested that the octapeptide SEQ ID NO:2: QMTPVNPG, like its parent protein and precursor 34-mer peptide (Wu et al. 1985; Eisele et al. 2001), aggregated during prolonged storage in the lyophilized state and only partially dissociated during chromatography, and that the monomeric form of the peptide was the active species. While not especially hydrophobic, the peptide does carry a net charge of only +1 at neutral pH, and taken together with the chromatography and urea evidence, it is reasonable to conclude that hydrophobicity played a role in its aggregation.

In addition to aggregation, small peptides such as octapeptide SEQ ID NO:6: EMTPVNPG or SEQ ID NO:2: QMTPVNPG have structural flexibility that allows them to attain a variety of different structural conformations. Since it was thought unlikely that all structural conformers of octapeptide SEQ ID NO:6: EMTPVNPG or SEQ ID NO:2: QMTPVNPG would be biologically active, it seemed appropriate to employ the strategy of conformational constraint in an effort to produce stable analogs. Therefore, cyclic analogs were generated to limit the number of conformers. Also hydrophilic analogs were generated to reduce the aggregation potential of the peptide by minimizing possible hydrophobic interactions discussed above.

Figure 3A:
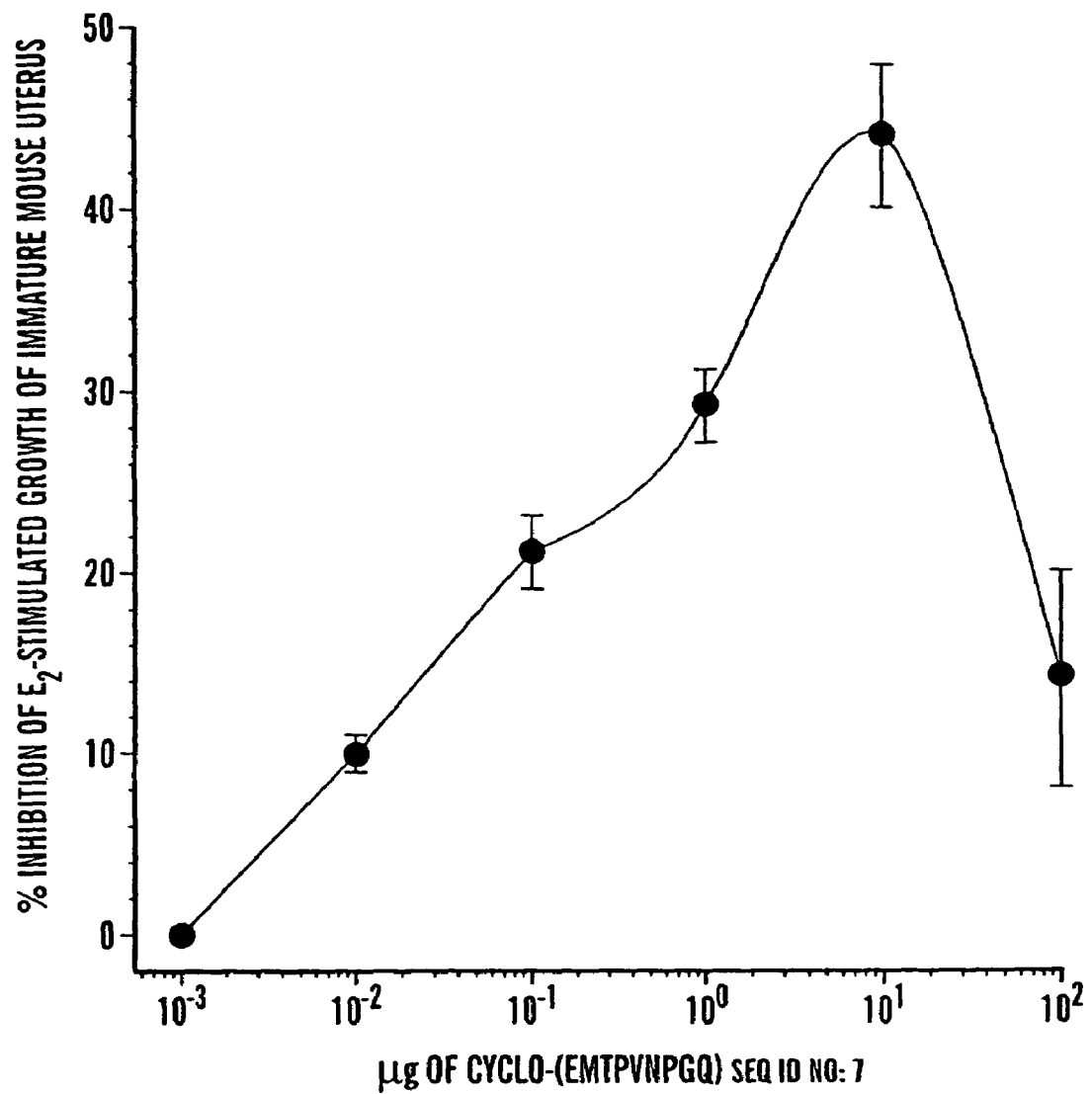
FIGS. 3a and 3b illustrate the anti-uterotrophic activity of cyclo-(SEQ ID NO:7: EMTPVNPGQ).
Figure 3B:
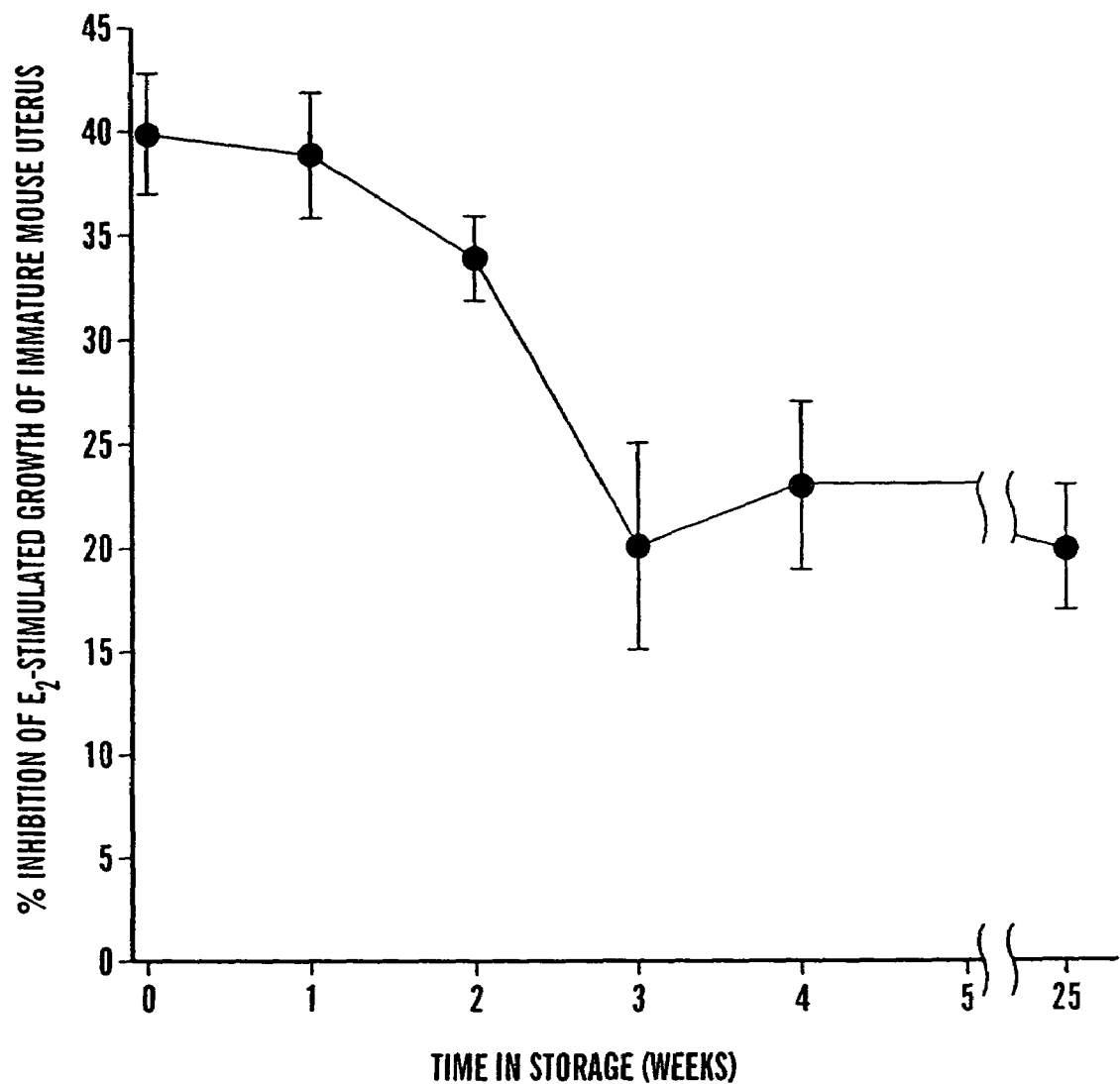

A linear peptide precursor for a potential cyclic peptide analog was synthesized by adding a glutamine residue to the C-terminus of the native octapeptide. This strategy provides a number of advantages: a) the glycine residue, shown earlier to be essential for biological activity (Mesfin et al. 2000), would not be involved in a cyclizing peptide bond, thereby retaining a conformation more like that in the native protein; b) addition of glutamine to the C-terminus and retention of glutamic acid at the N-terminus maintains a charge (−1) on the peptide after cyclization which may be advantageous in diminishing hydrophobically-induced aggregation; and c) the allyl-protection of the C-terminal amino acid facilitates the chemistry necessary to effect cyclization. This linear nonapeptide (SEQ ID NO:7: EMTPVNPGQ) was found to inhibit the estrogen-stimulated growth of mouse uterus with maximal inhibition at dose of 1 μg/mouse. Thus adding a glutamine residue to the C-terminal of octapeptide SEQ ID NO:6: EMTPVNPG did not diminish its biological activity. Cyclo-(SEQ ID NO:7: EMTPVNPGQ) was then synthesized by a head-to-tail cyclization reaction of the precursor nonapeptide as described in the Materials and Methods section. Cyclo-(SEQ ID NO:7: EMTPVNPGQ) exhibited dose dependent inhibition of estrogen-stimulated growth of immature mouse uterus with maximal inhibitory activity at a dose of 10 μg per mouse (FIG. 3a) and was also very active at the optimal dose of the linear peptides (1 μg). Nevertheless, storage experiments indicated that this cyclized peptide had somewhat extended but still rather limited shelf-life (FIG. 3b). After prolonged storage of six months, cyclo-(SEQ ID NO:7: EMTPVNPGQ) exhibited significant, albeit not optimal, biological activity (FIG. 3b). Treatment of aged cyclo-(SEQ ID NO:7: EMTPVNPGQ) with 4 M urea restored the optimal biological activity which suggested that the cyclic peptide might also have aggregated during storage in the lyophilized state.

Figure 4A:
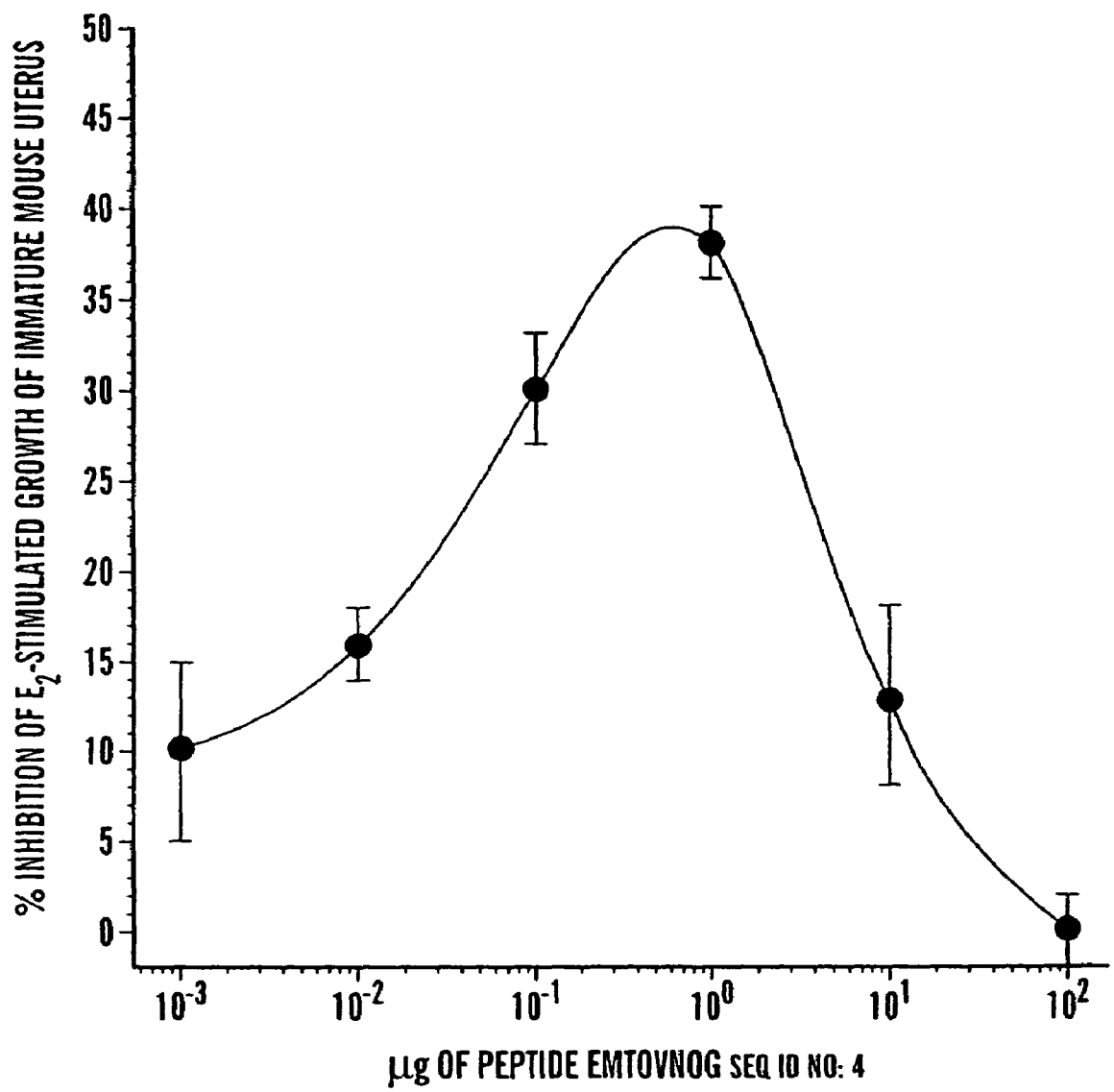
FIGS. 4a and 4b illustrate the anti-uterotrophic activity of peptide with hydroxyproline substituted for proline.
Figure 4B:
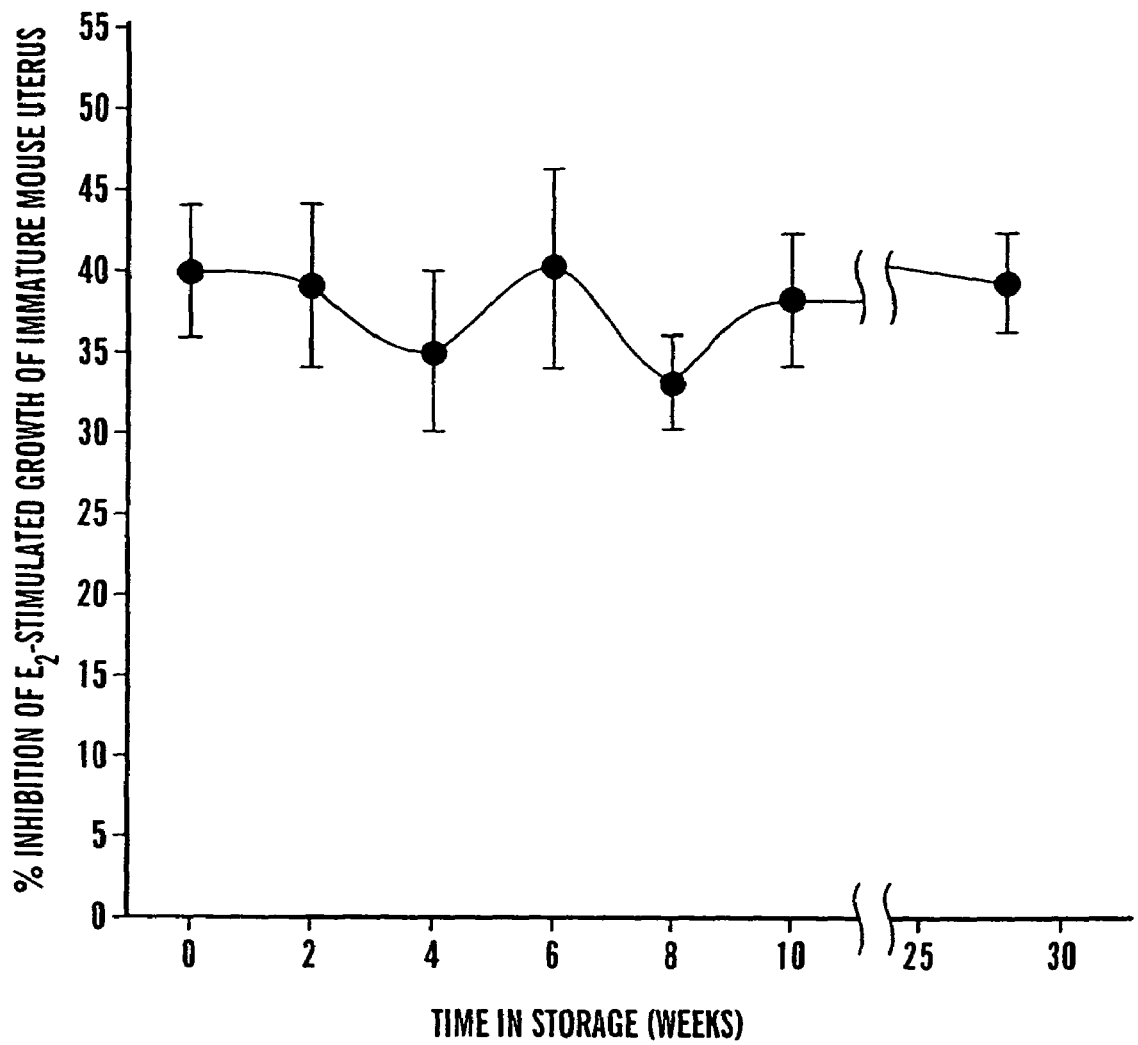
Figure 5:
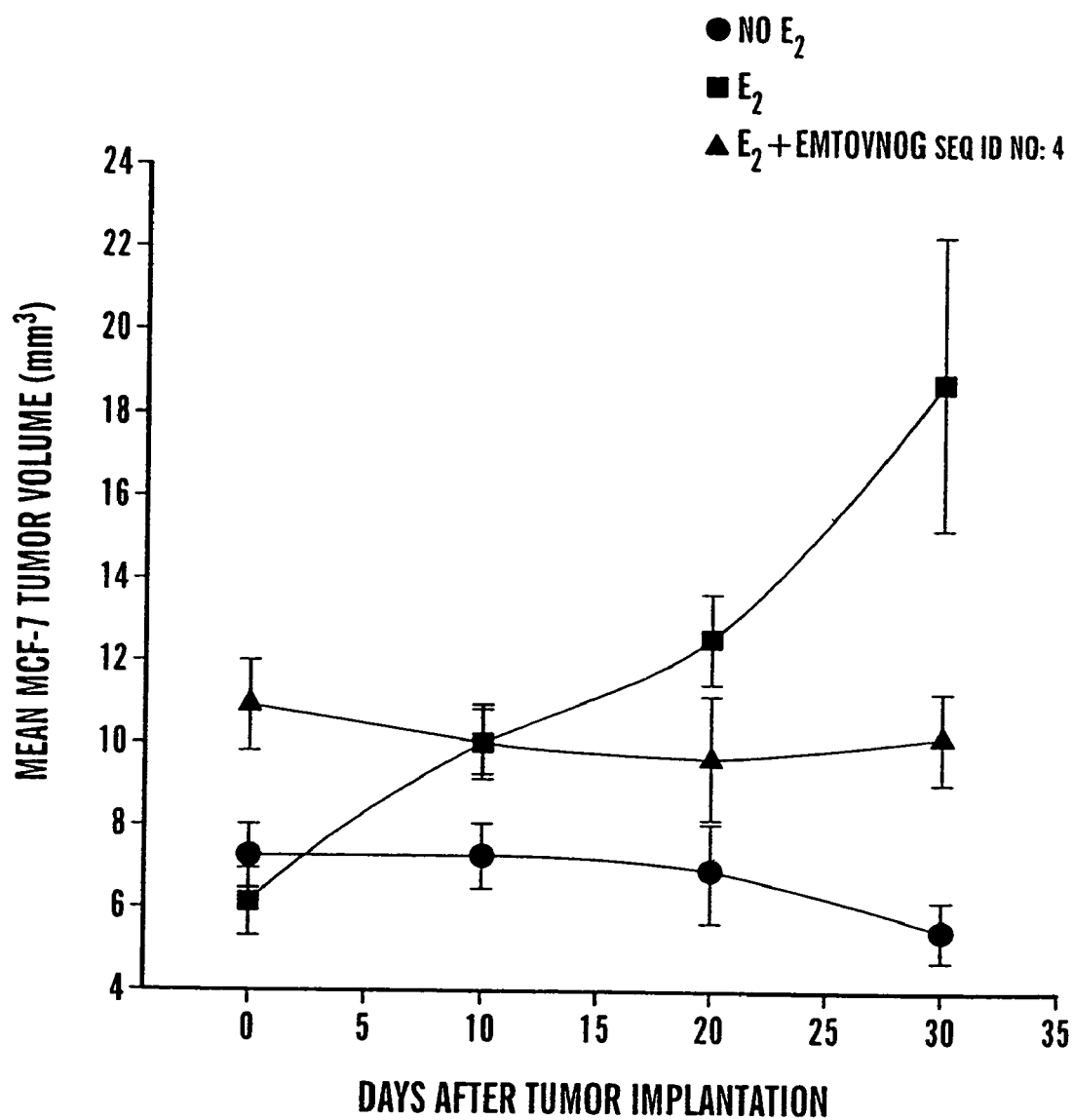
FIG. 5 illustrates the anti-estrotrophic activity of hydroxyproline-substituted linear peptide against MCF-7 human breast cancer xenografts. There were five to eight replicate mice per treatment group. Estrogen was provided via a slow release pellet implanted subcutaneously. Peptide was given twice a day i.p. at a dose of 1 µg per mouse. Tumor volumes in each mouse were measured at the time of tumor implantation and at 10-day intervals thereafter during survival laparotomies. At 30 days after tumor implantation, tumor volumes in the $E_2$+peptide group were significantly different from tumor volumes in the $E_2$ alone group, $p \leq 0.05$; Wilcoxon ranks-sum test.

In order to generate a more hydrophilic analog, the linear octapeptide SEQ ID NO:4: EMTOVNOG, where O is hydroxyproline, was produced. Like the native octapeptide, this more hydrophilic species exhibited dose dependent inhibition of estrogen-stimulated growth of immature mouse uterus with maximal effect at a dose of 1 μg per mouse (FIG. 4a). This result showed that the substitution (proline to 4-hydroxyproline) did not affect biological activity. Of critical importance, this hydrophilic octapeptide exhibited indefinite shelf-life when tested in the immature mouse uterine growth assay (FIG. 4b). Further, octapeptide SEQ ID NO:4: EMTOVNOG inhibited the estrogen-dependent growth of MCF-7 human breast cancer xenografts indicating that peptide activity extended to human breast cancer tissue (FIG. 5).

Figure 6A:
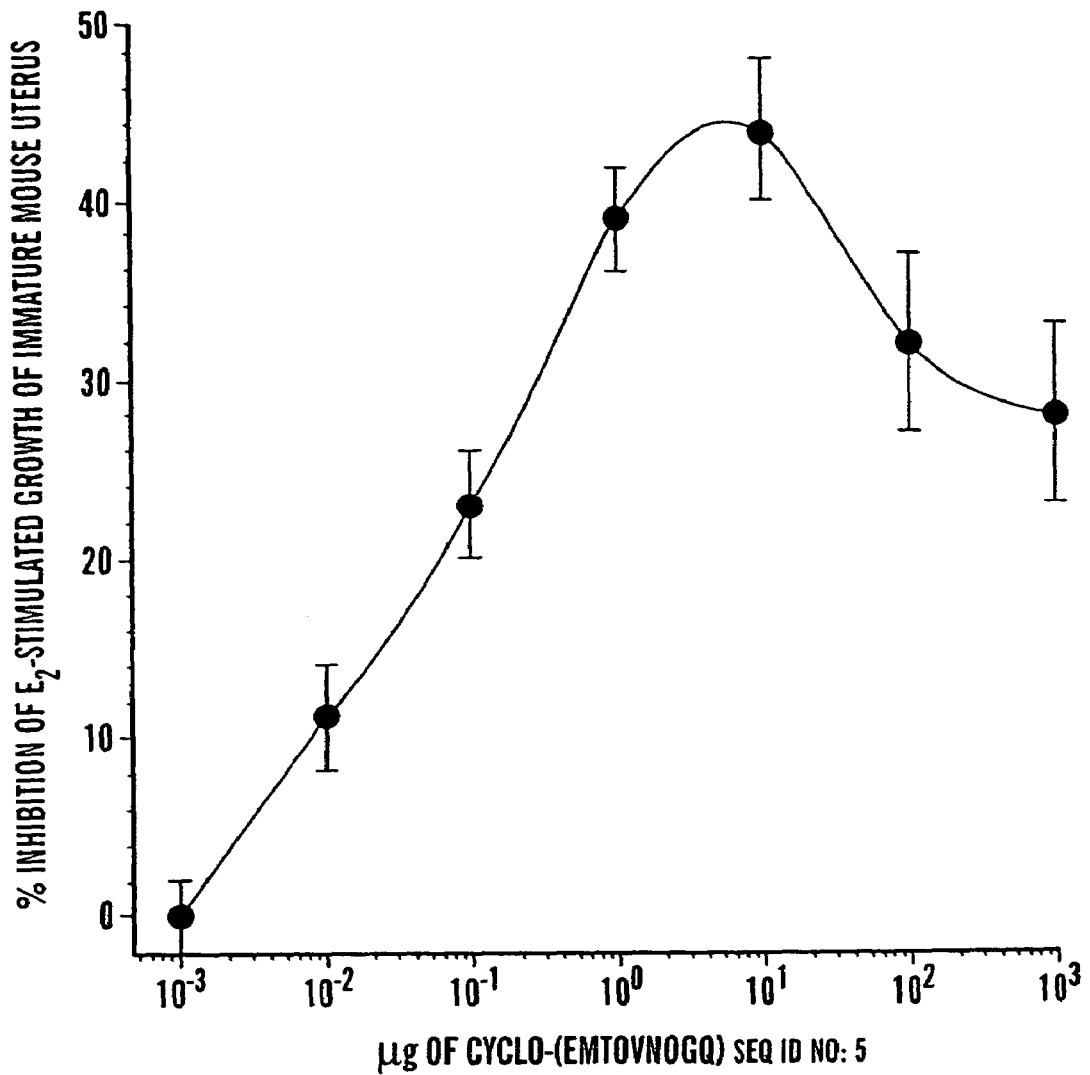
FIGS. 6a and 6b illustrate the anti-uterotrophic activity of cyclized peptide with hydroxyproline substituted for proline.
Figure 6B:
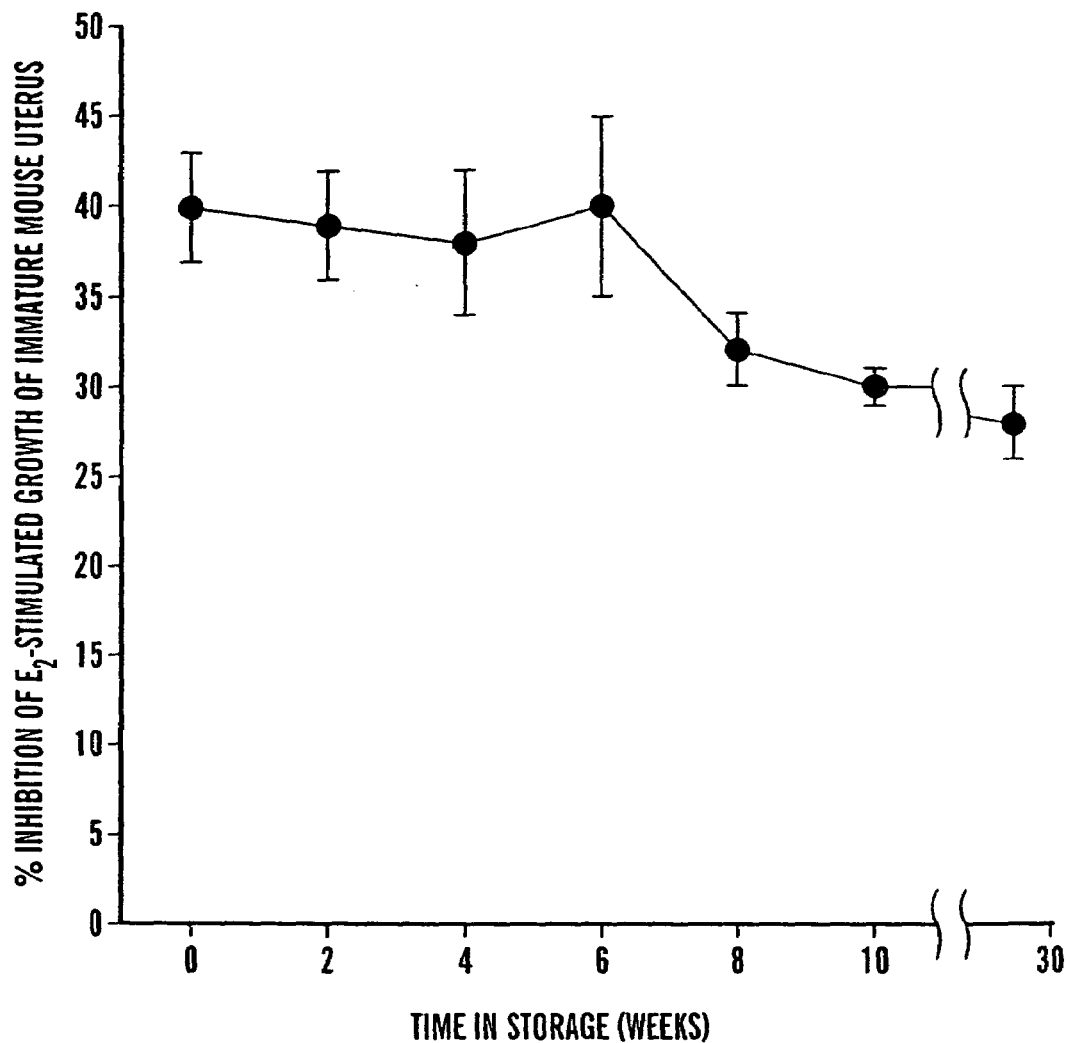
Figure 7:
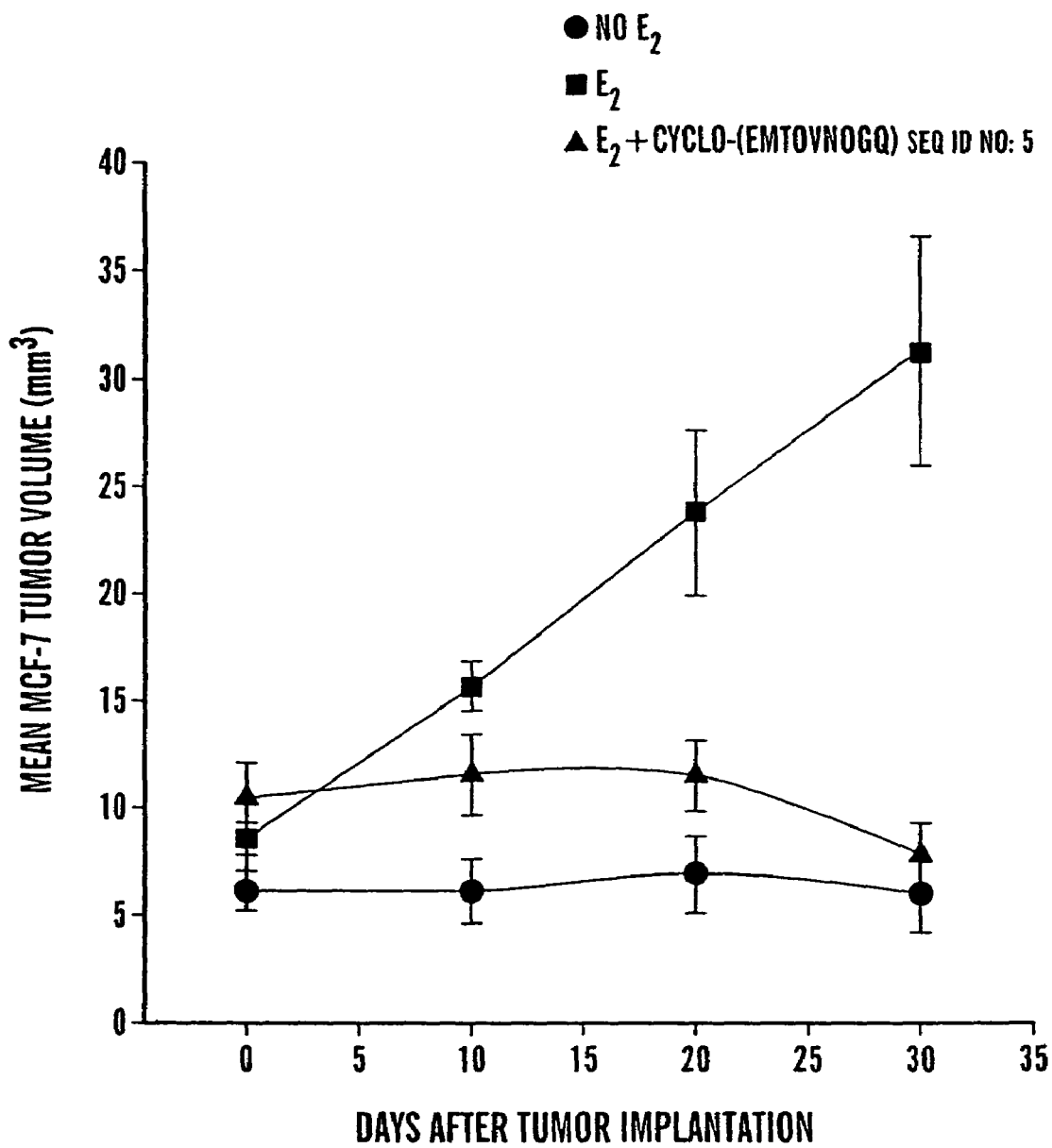
FIG. 7 illustrates the anti-estrotrophic activity of cyclized peptide with hydroxyproline substituted for proline against MCF-7 human breast cancer xenografts. Experimental protocol is described in legend to FIG. 5 and Materials and Methods. At 20 days and 30 days after tumor implantation tumor volumes in the $E_2$+peptide group were significantly different from tumor volumes in the $E_2$ alone group, $p<0.05$; Wilcoxon ranks-sum test.

Cyclo-(SEQ ID NO:5: EMTOVNOGQ) was synthesized by head-to-tail cyclization of the precursor nonapeptide as described in the Materials and Methods section. This analog incorporates conformational constraint as well as hydrophilic substitution of amino acids. Cyclo-(SEQ ID NO:5: EMTOVNOGQ) exhibited dose dependent inhibition of estrogen-stimulated growth of immature mouse uterus with the maximum inhibitory activity at a dose of 10 μg per mouse (FIG. 6a). Interestingly, this peptide retained significant anti-estrotrophic activity at doses higher than 10 μg/mouse, leading to a rather broad active dose range. There was no evidence of toxicity to the mice, even at an effective dose of 1 mg/mouse. Furthermore, storage experiments indicated that cyclo-(SEQ ID NO:5: EMTOVNOGQ) had indefinite shelf-life (FIG. 6b). This peptide was therefore tested for anti-breast cancer activity, and like the linear form it significantly inhibited the estrogen-dependent growth of MCF-7 human breast cancer xenografts (FIG. 7).

Figure 8:
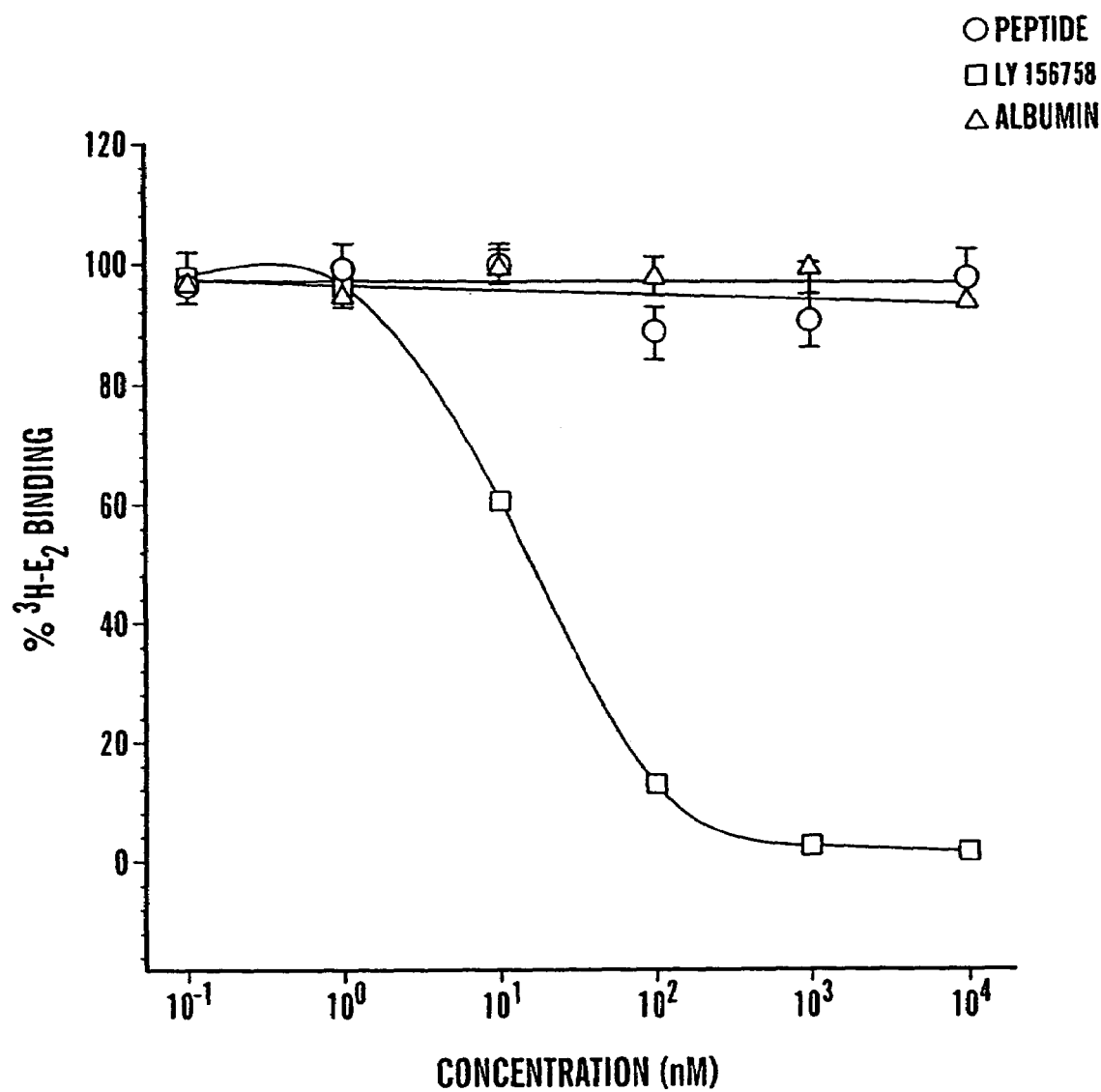
FIG. 8 illustrates the effect of linear hydroxyproline-substituted peptide on binding of $E_2$ to its receptor. Rabbit uterine cytosol was used as a source of estrogen receptor. All incubations were performed in triplicate, each containing 100 µl of cytosol, 20 µl of 10 nM 6,7-$^3$H estradiol (50 Ci/mmol), and 80 µl of test agent at the final concentrations indicated on the abscissa. Details of the assay are described in Materials and Methods. Concentration of [$^3$H]$E_2$-complex with receptor in the presence of different concentrations of test agent is expressed as a percentage of the amount of complex formed in the absence of test agent.

As shown in FIG. 8, the linear hydroxyproline-containing octapeptide did not interfere with estradiol binding to its receptor over a broad peptide concentration range, whereas raloxifene at a concentration of 100 nM completely inhibited this association.

The results of this study demonstrated that rational design approaches led to stepwise improvements in the therapeutic usefulness of an anti-estrotrophic peptide derived from AFP. The native peptide, SEQ ID NO:6: EMTPVNPG, and an analog with a minor modification, SEQ ID NO:2: QMT-PVNPG, were problematic in that they lost their antiestrotrophic activity after a relatively short time of four to five weeks in storage. The urea as well as the chromatography data suggested that monomeric units of these peptides were aggregating during storage, leading to biologically inactive oligomers. By mass spectrometry analysis, there was no evidence of other possible changes such as asparagine deamidation, methionine oxidation, or pyroglutamate formation to account for loss in biological activity. In these octapeptides, it is likely that the hydrocarbon side chains of proline and valine created a hydrophobic pocket that associated with like pockets on adjacent monomers resulting in aggregation during storage. However, by increasing the peptide's hydrophilicity by replacing the two prolines with 4-hydroxyprolines, this hydrophobic interaction was apparently impeded since the biological activity of the 4-hydroxyproline containing peptide did not diminish over time in storage. The net result is that this minor but novel design modification yielded a peptide with indefinite shelf life which is eminently more translatable to the clinic in comparison to a peptide with only four weeks of shelf life.

A variety of excipients were evaluated as cryoprotectants and lyoprotectants for the native AFP-derived octapeptide SEQ ID NO:6: EMTPVNPG. Mannitol as well as dodecylmaltoside significantly prolonged shelf-life of the peptide, whereas sucrose did not do so.

It was considered that cyclization of this peptide would limit its flexibility and thereby reduce the number of possible conformations it could assume and that this may in turn broaden the effective dose range assuming that different conformations are not all biologically active and may in fact interfere with each other. However, we did not want to lose the advantages accrued from the hydroxyproline substitutions, and therefore the two approaches were combined. This was remarkably successful. The cyclic, hydrophilic analog, cyclo-(SEQ ID NO:5: EMTOVNOGQ), has full biological activity and indefinite shelf-life. What was even more beneficial about this analog was that its dose-response curve was substantially broadened greatly increasing the range of doses over which the agent was effective. With linear peptide the dose-response curve was biphasic. A dose of 1.0 μg/mouse produced maximal inhibition, while higher doses showed reduced anti-estrotrophic activity. By contrast, with cyclo-(SEQ ID NO:5: EMTOVNOGQ) the shape of the dose-response curve was sigmoidal, with 1.0 μg up to 1.0 mg per mouse providing similar antiestrotrophic activity. This greatly expands the active dose range and increases the probability of maintaining an effective dose in humans.

The finding that both linear and cyclized peptides completely stopped the growth of human MCF-7 breast cancer xenografts is highly significant and certainly demonstrates the relevance of these peptides to breast cancer therapeutics. The magnitude of their inhibitory effect was similar to that of tamoxifen which was also shown to stop MCF-7 breast cancer xenograft growth in an earlier study (Bennett et al. 1998). However, their mechanism of action seems to be different from that of tamoxifen, in that they do not interfere with estrogen binding to its receptor. This opens the possibility of combining these agents with tamoxifen or using them in place of tamoxifen when, as so often happens, an estrogen receptor positive breast cancer becomes resistant to tamoxifen (Howell et al. 1995).

EXAMPLE II

Prevention of Growth of Estrogen-Dependent Human Breast Cancers Sensitive and Resistant to Tamoxifen.

An 8-mer peptide (SEQ ID NO:4: EMTOVNOG) derived from alpha-fetoprotein (AFP) was compared to tamoxifen for activity against growth of human breast cancer xenografts implanted in immune-deficient mice. Both peptide and tamoxifen prevented growth of estrogen-receptor-positive MCF-7 and T47D human breast cancer xenografts. A subline of MCF-7, made resistant to tamoxifen by a six-month exposure to this drug in culture, was found to be resistant to tamoxifen in vivo. Peptide-completely prevented the xenograft growth of this tamoxifen-resistant subline of MCF-7. Neither peptide nor tamoxifen were effective in slowing the xenograft growth of the estrogen-receptor-negative MDA-MB-231 human breast cancer. A worrisome toxicity of tamoxifen is its hypertrophic effect on the uterus. In this study, tamoxifen was shown to stimulate the growth of the immature mouse uterus in vivo, and the peptide significantly inhibited tamoxifen's uterotrophic effect. The mechanism of action of peptide is different from that of tamoxifen in that the peptide does not interfere with the binding of [$^3$H]estradiol to the estrogen receptor. In conclusion, AFP-derived peptide appears to be a novel agent that interferes with the growth of tamoxifen-sensitive as well as tamoxifen-resistant estrogen-receptor-positive human breast cancers; it inhibits the uterotrophic side effect of tamoxifen; and thus it can be used in combination with or in place of tamoxifen for treatment of estrogen-receptor-positive human breast cancers.

Figure 9A:
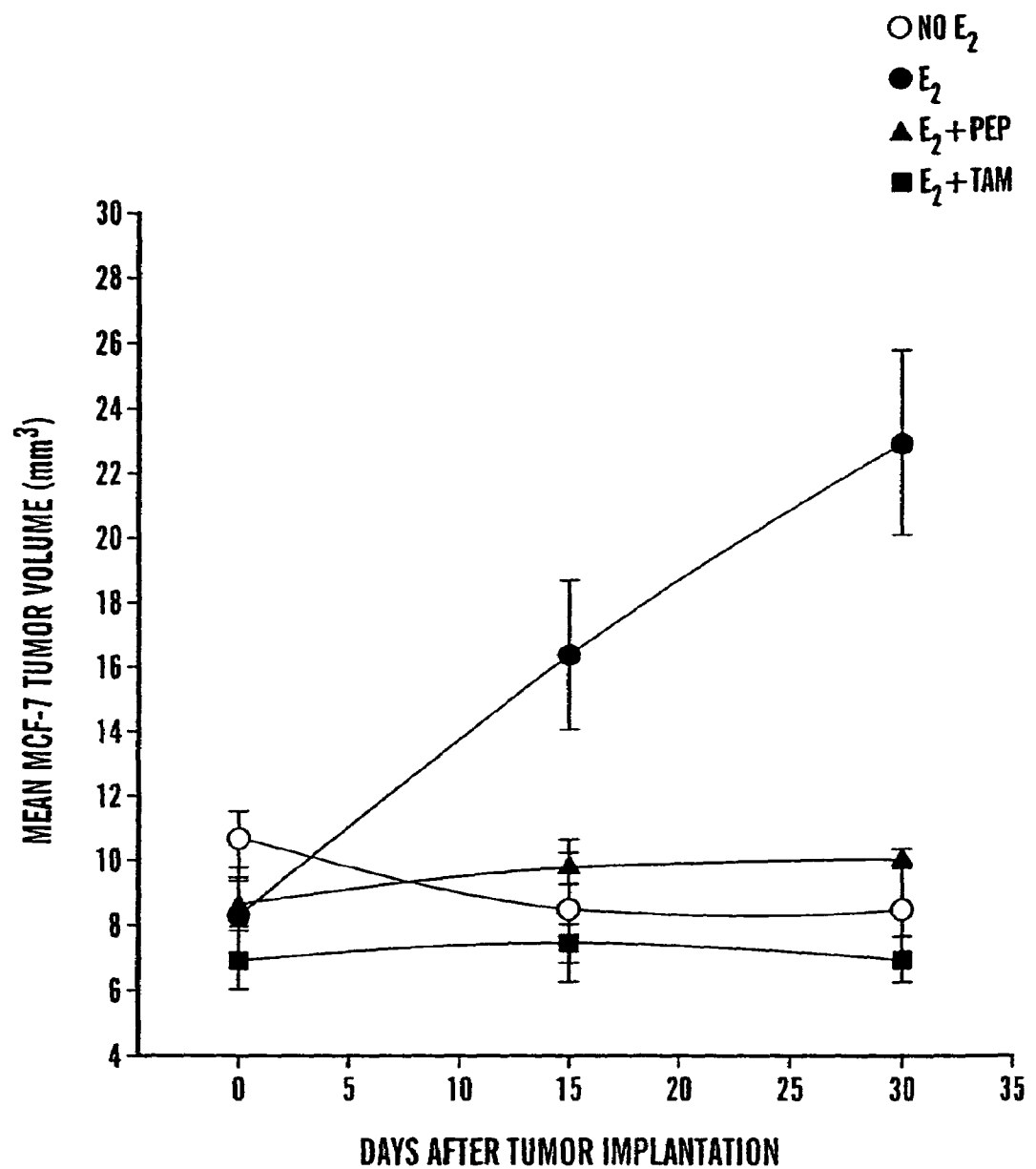
FIGS. 9a and 9b illustrate the effect of AFP-derived peptide on growth of estrogen-receptor-positive MCF-7 and MCF-7/Tam human breast cancer xenografts. Tumors were implanted as described in Materials and Methods. Estrogen (●) was provided via a slow-release pellet of estradiol ($E_2$) implanted s.c. ▲ Peptide was given twice a day i.p. at a dose of 1 µg per injection. ■ Tamoxifen was given once a day i.p. at a dose of 50 µg per mouse. Tumor volumes in each mouse were measured at the time of tumor implantation, again at day 15 after tumor implantation during survival laparotomy and again at day 30 after tumor implantation during necropsy. There was a minimum of 5 mice per group.
Figure 9B:
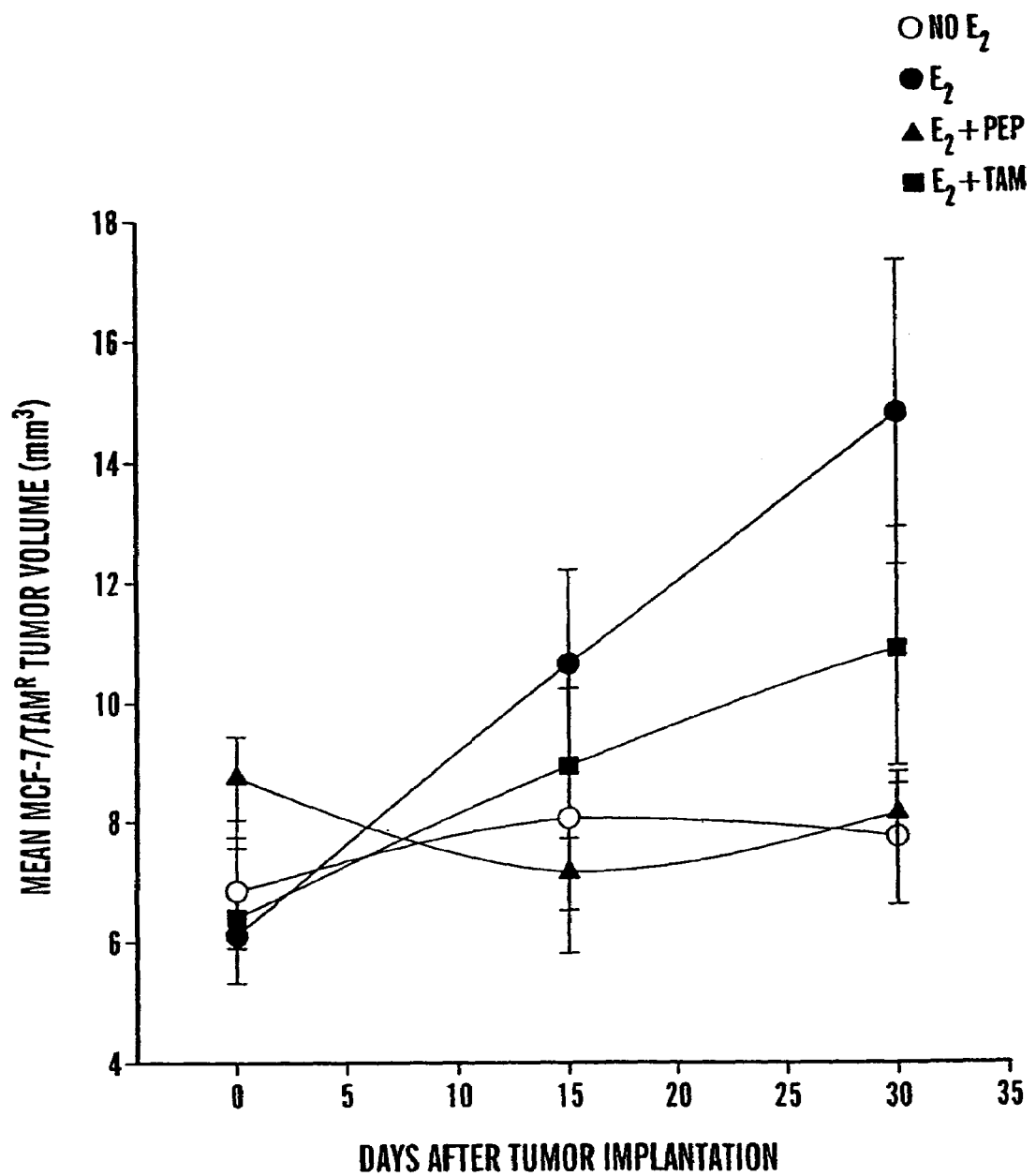
Figure 10:
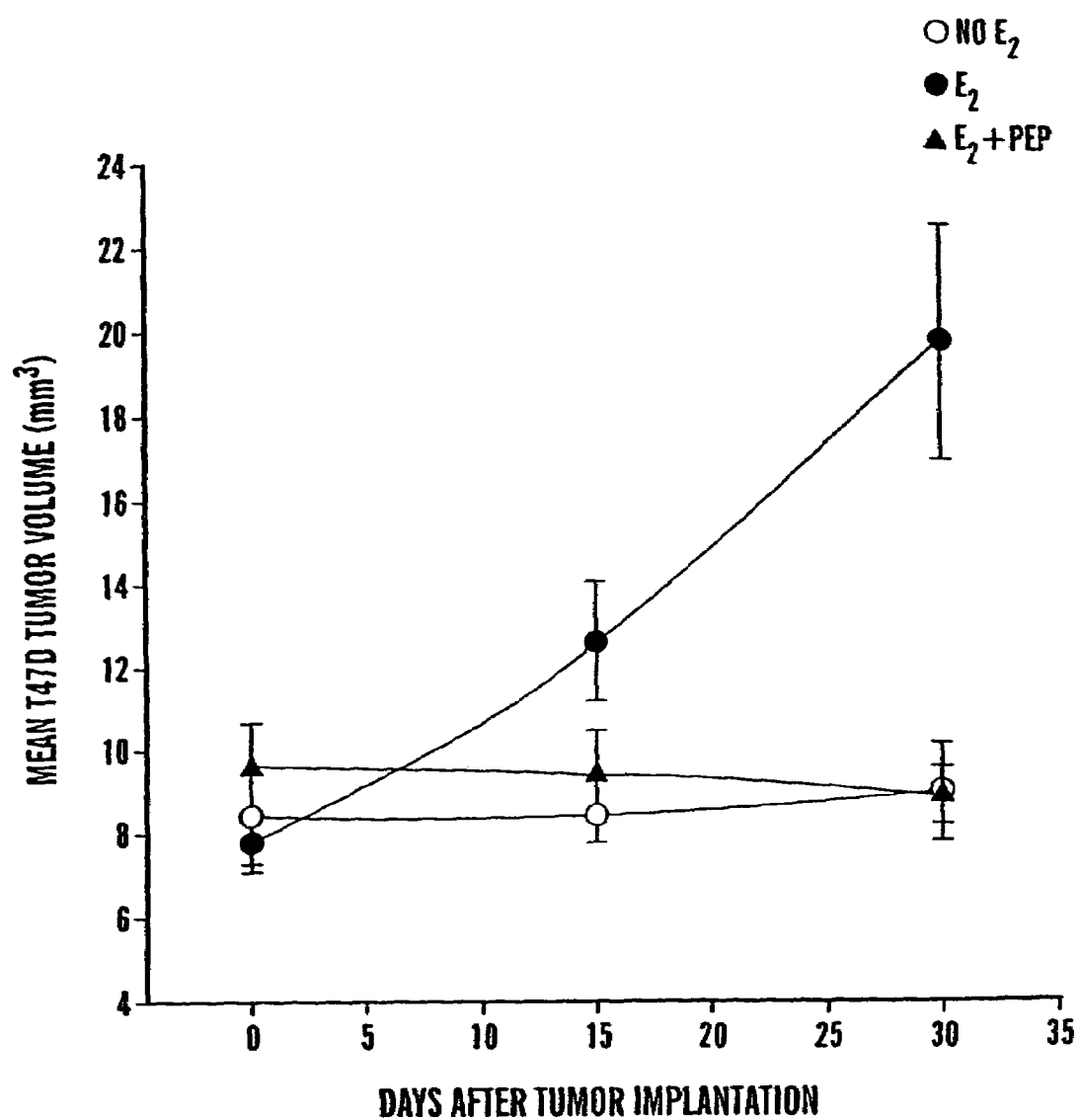
FIG. 10 illustrates the effect of AFP-derived peptide on growth of estrogen-receptor-positive T47D human breast cancer xenografts. See legend to FIGS. 9a and 9b for experimental protocol. At day 30 after tumor implantation, tumor volumes in the $E_2$+Pep group were significantly different from tumor volumes in the $E_2$ alone group, $p<0.05$, Wilcoxon Ranks Sum Test.
Figure 11:
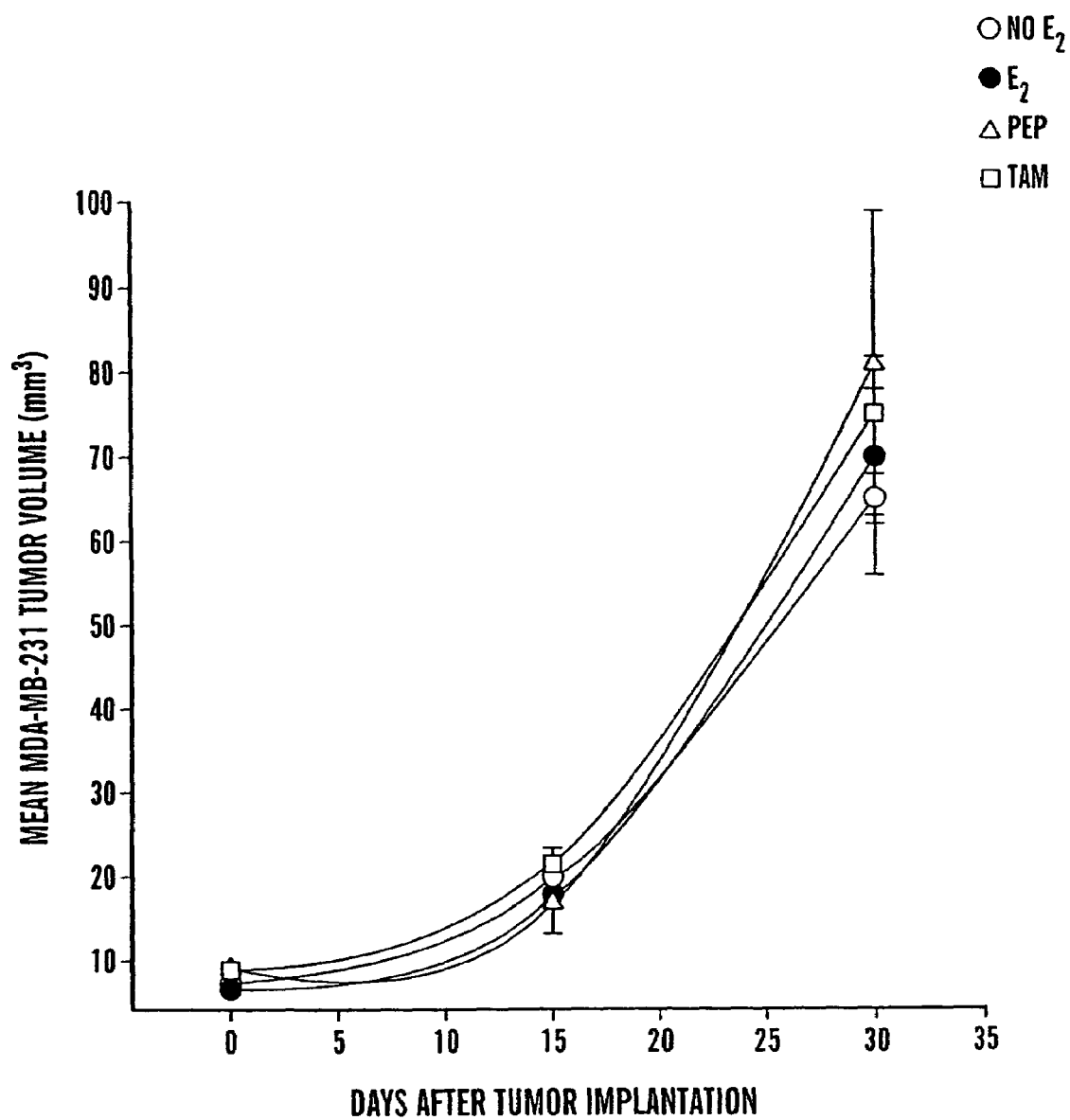
FIG. 11 illustrates the effect of AFP-derived peptide on growth of estrogen-receptor-negative MDA-MB-231 human breast cancer xenografts. See legend to FIGS. 9a and 9b for experimental protocol. There were no differences in tumor volumes between any of the groups.

It was determined in a screening assay of the inhibition of $E_2$-stimulated growth of immature mouse uterus by AFP-derived peptide that an effective anti-estrotrophic dose of SEQ ID NO:4: EMTOVNOG was 0.1 μg to 1.0 μg per mouse. Also, preliminary pharmacokinetic studies suggested that the biological half-life of this peptide in these mice was two to three hours. Therefore, for the breast cancer xenograft studies, it was deemed reasonable to administer this peptide twice a day at a dose of 1.0 μg per i.p. injection into tumor-bearing SCID mice. The ER+ MCF-7 human breast cancer was used as a first step in evaluating the effectiveness of this peptide against human breast cancer. As shown in FIG. 9a, MCF-7 xenografts were completely dependent on estrogen for growth in SCID mice. They underwent an approximate threefold increase in tumor volume in the presence of a slow-release $E_2$ implant during the 30-day observation. Without $E_2$ supplementation, there was no tumor growth. When $E_2$-supplemented mice were given twice-daily injections of 1 μg of peptide, there was no significant increase in tumor volume over the 30-day observation period. Similarly, when $E_2$-supplemented tumors were given once-daily injections of 50 μg of tamoxifen, there was no increase in tumor volume. When a subline of MCF-7 that had been made resistant to tamoxifen in cell culture was used, a rather provocative outcome was obtained. Xenografts of this subline were still completely dependent on $E_2$ for growth (FIG. 9b). With $E_2$ supplementation, they grew somewhat slower than the parent line, approximately doubling in tumor volume over the 30-day observation period. Interestingly, tamoxifen was only minimally effective in retarding the growth of this subline, such that at day 30 after tumor implantation, the tumor volume in the $E_2$ plus tamoxifen group was not significantly smaller than that found in the group receiving $E_2$ only (FIG. 9b). In contrast, peptide completely stopped the growth of this tamoxifen-resistant MCF-7 subline. The peptide was also tested on ER+ T47D human breast cancer. Like the MCF-7, T47D xenografts were completely dependent on $E_2$ supplementation for growth (FIG. 10) and more than doubled in tumor volume over the 30-day observation period. Daily treatment with peptide during this time interval completely prevented tumor growth (FIG. 10). An ER-human breast cancer, MDA-MB-231, was then tested for sensitivity to peptide. This tumor grew independent of estrogen supplementation and demonstrated a rather aggressive growth rate during the second two weeks of the observation period (FIG. 11). Daily treatment with peptide had no effect on the growth of this tumor at any time during the 30 day observation period (FIG. 11). Similarly, tamoxifen did not affect the growth of this ER− tumor.

Figure 12:
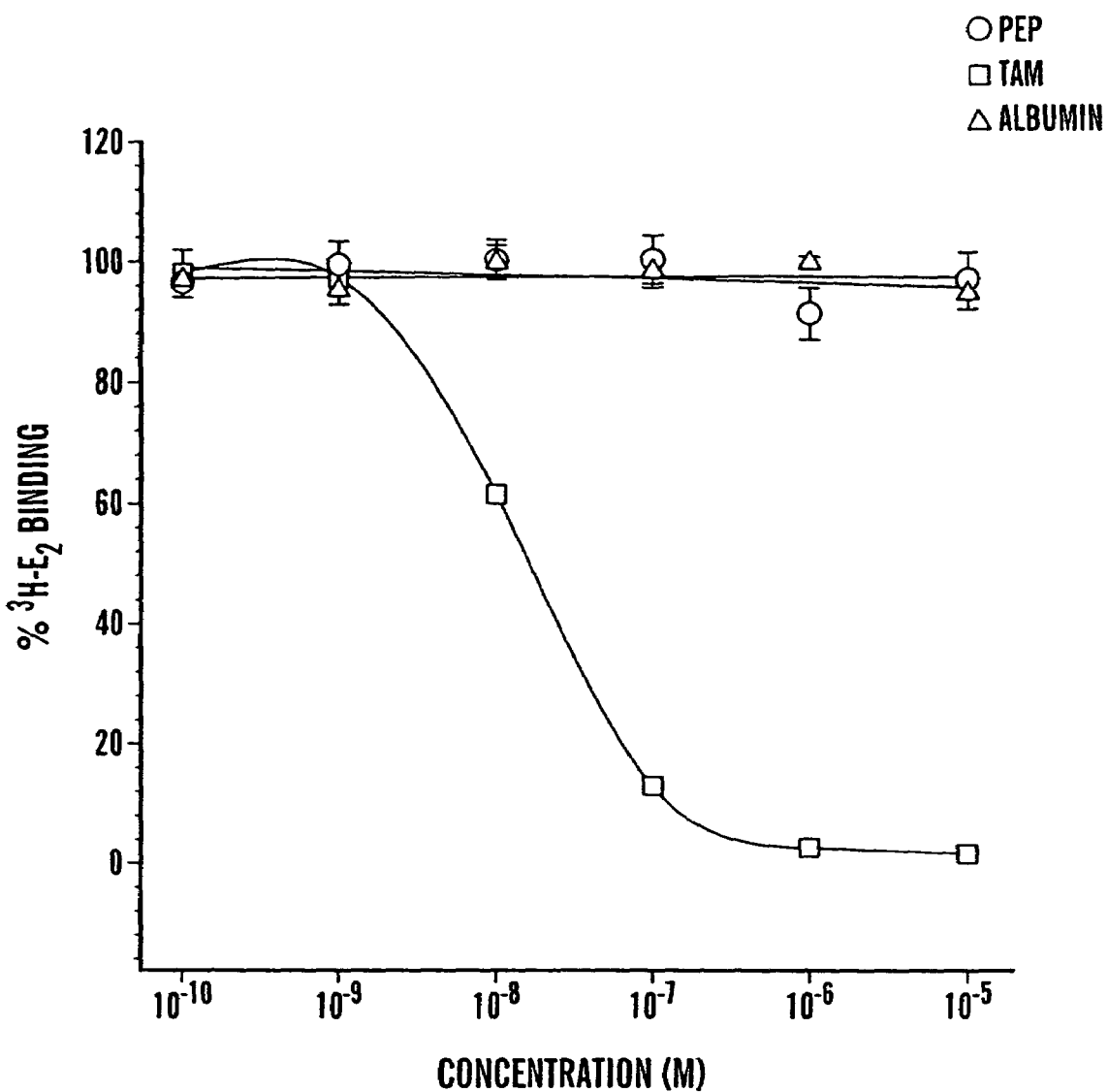
FIG. 12 illustrates the effect of AFP-derived peptide on binding of $E_2$ to its receptor. Rabbit uterine cytosol was used as a source of estrogen receptor. All incubations were performed in triplicate, each containing 100 µl of cytosol, 20 µl of 10 nM 6,7-$^3$H estradiol (50 Ci/mmol), and 80 µl of test agent at the final concentrations indicated on the abscissa. Concentration of [$^3$H]$E_2$-complex with receptor in the presence of different concentrations of test agent is expressed as a percentage of the amount of complex formed in the absence of test agent.

It appears that peptide interferes with E-dependent, but not E-independent, breast cancer growth. As a first step in evaluating the mechanism of action of this peptide, it was compared to tamoxifen as a competitor of $E_2$ for binding to ER. As shown in FIG. 12, tamoxifen exhibits its well documented interference with $E_2$ binding to ER. The $IC_{50}$ and IC-100 for tamoxifen were $5\times10^{-8}$ M and $5\times10^{-7}$ M respectively. In contrast, peptide produced no interference with $E_2$ binding to ER over a peptide concentration range of $10^{-10}$ M to $10^{-5}$ M. Thus the mechanism by which peptide interferes with response to estrogen is clearly different from that of tamoxifen.

Figure 13A:
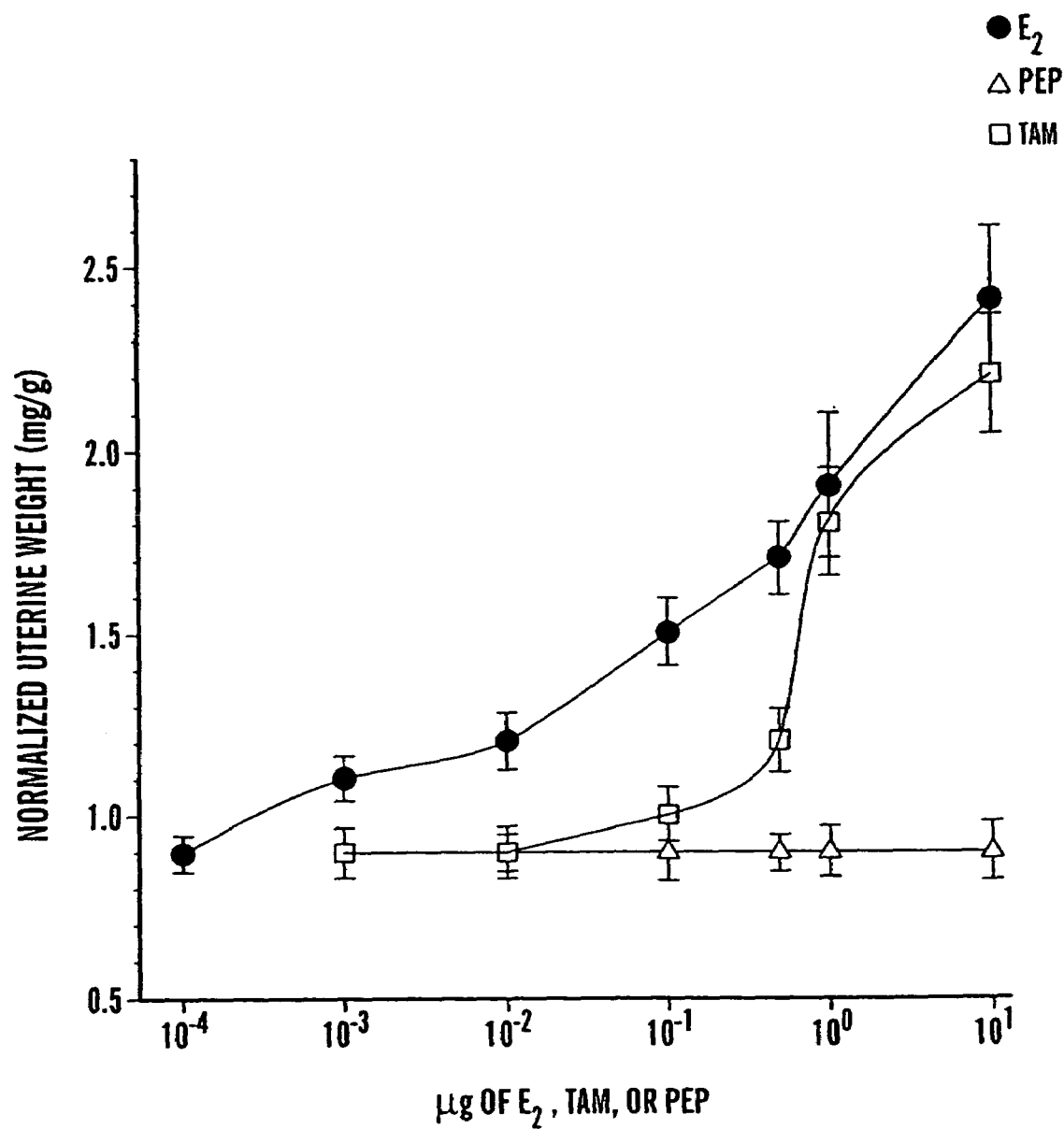
FIG. 13a shows the effect of estradiol ($E_2$), AFP-derived peptide (Pep) and tamoxifen (Tam) on the growth of the immature mouse uterus. The assay procedure is described in the Materials and Methods. Various doses indicated on the abscissa of each test agent were injected i.p. Twenty-two hours later uteri were harvested and weighed. Mean normalized uterine weights (mg uterine weight/g mouse body weight) for each group are shown on the ordinate.
Figure 13B:
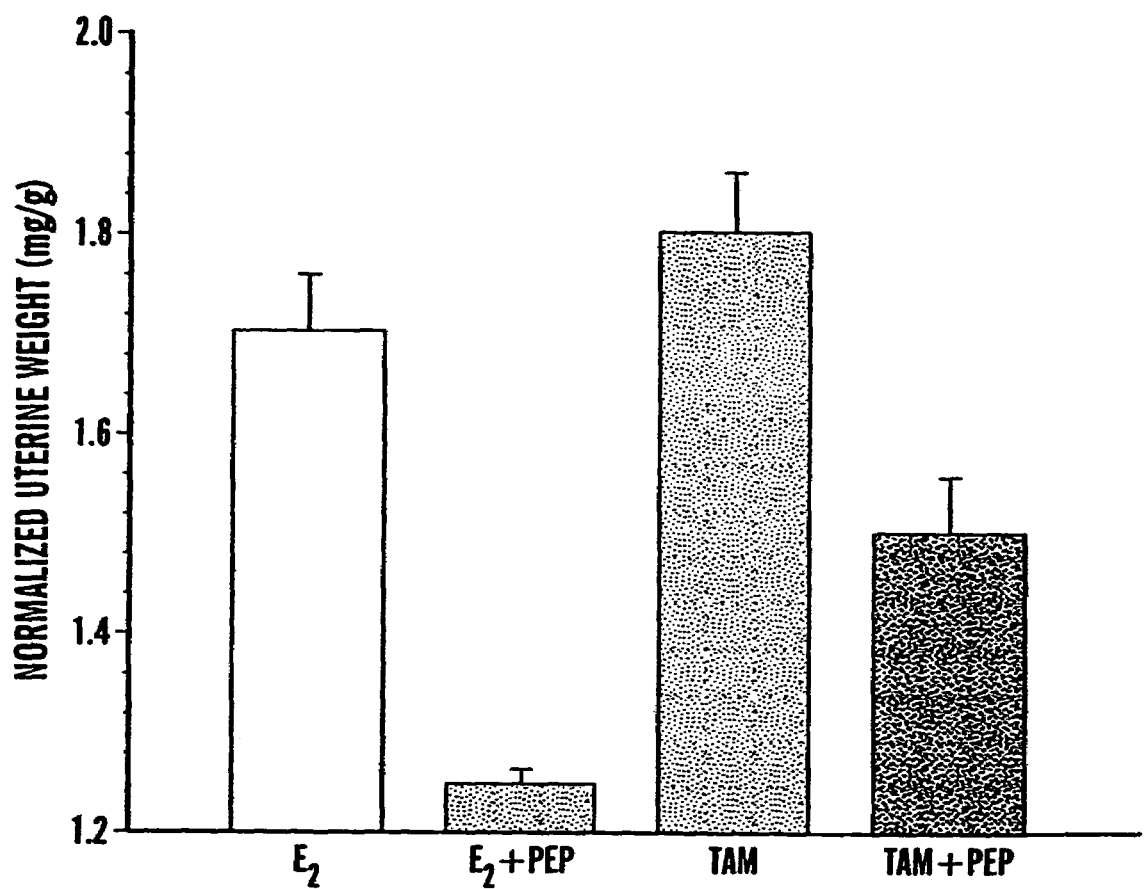
In FIG. 13b, Pep (1 µg) or vehicle (saline, 0.2 ml) were injected i.p. One hour later $E_2$ (0.5 µg) or Tam (1.0 µg) were injected i.p. Twenty-two hours later uteri were harvested and weighed. Normalized uterine weights in the $E_2$+Pep and Tam+ Pep groups were significantly different respectively from normalized uterine weights in the $E_2$ group and Tam group, $p<0.05$, Wilcoxon Ranks Sum Test.

A troublesome side effect of tamoxifen in women has been its hypertrophic effect on the uterus (Assikis et al. 1995). It is likewise an estrogen agonist in the murine uterus. As shown in FIG. 13a, tamoxifen stimulated the growth of immature mouse uterus by 50% at a dose of 1 μg/mouse. Tamoxifen's potency was approximately one-tenth that of $E_2$, but nevertheless, FIG. 13a reaffirms that tamoxifen acts as an estrogen agonist on the murine uterus, even though it antagonizes the effect of estrogen on cancer of the breast. Peptide, on the other hand, had no uterotrophic effect whatsoever (FIG. 13a), even at a dose of 10 μg/mouse, which is tenfold greater than the dose employed to prevent breast cancer growth (FIGS. 9a, 9b and 11). Moreover, peptide inhibited the uterotrophic effect of tamoxifen as well as that of estradiol (FIG. 13b).

The results of this study demonstrate that a synthetic 8-mer peptide derived from AFP prevented the $E_2$-stimulated growth of human breast cancer xenografts, including an ER+ breast cancer line that had become resistant to tamoxifen during chronic exposure to this drug in culture. This acquired resistance is similar to what happens in patients whose cancers become resistant to tamoxifen during chronic treatment with this drug (Norris et al. 1999). The peptide had no effect on the growth of ER− breast cancer, which is consistent with the activity found with its parent protein, AFP (Bennett et al. 1998).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE I

Effect of urea on the biological activity of stored peptide.

| | Test Agent | Storage Time | % Inhibition of E2-Stimulated Growth of Immature Mouse Uterus ± SE [b] |
|---|---|---|---|
| I | Octapeptide SEQ ID NO:2: QMTPVNPG | Fresh | 38 ± 3 |
| II | Octapeptide SEQ ID NO:2: QMTPVNPG | Stored over 1 year | 0 ± 2 |
| III | II after Urea Treatment [a] | None | 34 ± 4 |
| IV | Scrambled Octapeptide | Fresh | 2 ± 5 |
| V | IV after Urea Treatment | None | 0 ± 4 |

[a] Peptides were dissolved in phosphate buffered saline pH 7.4 at a concentration of 200 μg/ml. They were then diluted to 20 μg/ml in 4 M urea and incubated at room temperature for one hour. After incubation they were diluted to 2 μg/ml in buffer and 0.5 ml of this preparation (1 μg) was injected into mice as described in legend to FIGS. 1a and 1b. This diluted dose of urea had no adverse effects on mice.
[b] Assessed as described in legend to FIG. 1a and 1b.

REFERENCES

Assikis, V. J., et al., Int J Gynecol Obstet 49:241–257 (1995).
Bauer, H. H., et al., Biochemistry 33:12276–12282 (1994).
Bennett, J. A., et al., Clin Cancer Res 4:2877–2884 (1998).
Christmanson, L., et al., Diabetologia 36:183–188 (1993).
Couinaud, C., et al., Ann Chir 27:151–156 (1973).
Eisele, L. E., et al., J Pept Res 57:29–38 (2001).
Fisher, B., et al., N Engl J Med 320:479–484 (1989).
Fisher, B., et al., J Natl Cancer Inst 90:1371–1388 (1998).
Gierthy, J. F., et al., J Cell Biochem 45:177–187 (1991).
Goss, P. E., et al., J Clin Oncol 19:881–894 (2001).
Halverson, K., et al., Biochemistry 29:2639–2644 (1990).
Hilbich, C., et al., J Mol Biol 218:149–163 (1991).
Hilbich, C., et al., J Mol Biol 228:460–473 (1992).
Howell, A., et al., Lancet 345:29–30 (1995).
Hughes, S. R., et al., Proc Natl Acad Sci USA 93:2065–2070 (1996).
Jacobson, H. I., et al., in *Biological Activities of Alpha-Fetoprotein*, eds. Mizejewski, G. J. and Jacobson, H. I., CRC Press, Inc., Boca Raton, Fla., pp. 94–100 (1989).
Jensen, E. V., et al., in *Cancer Medicine*, eds. Holland, J. F., et al., Williams & Wilkins, Baltimore, Md., pp. 1049–1060 (1996).
Kendrick, B. S., et al., J Pharm Sci 87:1069–1076 (1998).
Martin, M. B., et al., Breast Cancer Res Treat 31:183–189 (1994).
Mesfin, F. B., et al., Biochim Biophys Acta 1501:33–43 (2000).
Mizejewski, G. J., et al., Proc Natl Acad Sci USA 80:2733–2737 (1983).
Norris, J. D., et al., Science 285:744–746 (1999).
Nystedt, M., et al., Acta Oncol 39:959–968 (2000).
Richardson, B. E., et al., Am J Epidemiol 148:719–727 (1998).
Sluzky, V., et al., Proc Natl Acad Sci USA 88:9377–9381 (1991).
Sonnenschein, C., et al., J Natl Cancer Inst 64:1147–1152 (1980).
Wu, J. T., et al., Clin Chem 31:1692–1697 (1985).

What is claimed is:

1. A method of reducing estrogen-stimulated growth of cells in a subject, the method comprising exposing said cells to a peptide, comprising a sequence selected from the group consisting of:

| SEQ ID NO:4:  | EMTOVNOG;      |
| SEQ ID NO:5:  | EMTOVNOGQ;     |
| SEQ ID NO:8:  | EMTOVNPG;      |
| SEQ ID NO:9:  | EMTOVNPGQ;     |
| SEQ ID NO:10: | EMTPVNOG; and  |
| SEQ ID NO:11: | EMTPVNOGQ,     | and wherein said peptide has antiestrotrophic activity and is eight to twenty amino acids long.

2. The method of claim 1, comprising exposing the cells to tamoxifen before, during, or after exposing the cells to the peptide.

3. The method of claim 1, wherein said peptide is a dimeric peptide consisting of two peptides selected from the group consisting of SEQ ID NOS: 4–5, and 8–11.

4. The method of claim 3, wherein the dimeric peptide consists of SEQ ID NO: 4 and SEQ ID NO: 5.

5. The method of claim 1, wherein said peptide is a multimeric peptide consisting of three or more peptides selected from the group consisting of SEQ ID NOS: 4–5, and 8–11.

\* \* \* \* \*

UNITED STATES PATENT AND TRADEMARK OFFICE
CERTIFICATE OF CORRECTION

| | |
|---|---|
| PATENT NO. | : 7,132,400 B2 |
| APPLICATION NO. | : 10/990877 |
| DATED | : November 7, 2006 |
| INVENTOR(S) | : Thomas T. Andersen et al. |

It is certified that error appears in the above-identified patent and that said Letters Patent is hereby corrected as shown below:

Title page, item (73), the Assignee should be: "Albany Medical College" (US)
Albany, NY (US)

Signed and Sealed this
Second Day of August, 2011

David J. Kappos
*Director of the United States Patent and Trademark Office*

SEQUENCE LISTING

<160> NUMBER OF SEQ ID NOS: 11

<210> SEQ ID NO 1
<211> LENGTH: 34
<212> TYPE: PRT
<213> ORGANISM: Homo sapiens

<400> SEQUENCE: 1

Leu Ser Glu Asp Lys Leu Leu Ala Cys Gly Glu Gly Ala Ala Asp Ile
1               5                   10                  15

Ile Ile Gly His Leu Cys Ile Arg His Glu Met Thr Pro Val Asn Pro
            20                  25                  30

Gly Val

<210> SEQ ID NO 2
<211> LENGTH: 8
<212> TYPE: PRT
<213> ORGANISM: Homo sapiens

<400> SEQUENCE: 2

Gln Met Thr Pro Val Asn Pro Gly
1               5

<210> SEQ ID NO 3
<211> LENGTH: 9
<212> TYPE: PRT
<213> ORGANISM: Homo sapiens

<400> SEQUENCE: 3

Gln Met Thr Pro Val Asn Pro Gly Glu
1               5

<210> SEQ ID NO 4
<211> LENGTH: 8
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 4

Glu Met Thr Pro Val Asn Pro Gly
1               5

<210> SEQ ID NO 5
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp
<220> FEATURE:
<221> NAME/KEY: MOD_RES
<222> LOCATION: (7)
<223> OTHER INFORMATION: 4Hyp

<400> SEQUENCE: 5

Glu Met Thr Pro Val Asn Pro Gly Gln
1               5

```
<210> SEQ ID NO 6
<211> LENGTH: 8
<212> TYPE: PRT
<213> ORGANISM: Homo sapiens

<400> SEQUENCE: 6

Glu Met Thr Pro Val Asn Pro Gly
 1               5

<210> SEQ ID NO 7
<211> LENGTH: 9
<212> TYPE: PRT
<213> ORGANISM: Homo sapiens

<400> SEQUENCE: 7

Glu Met Thr Pro Val Asn Pro Gly Gln
 1               5

<210> SEQ ID NO 8
<211> LENGTH: 8
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp

<400> SEQUENCE: 8

Glu Met Thr Pro Val Asn Pro Gly
 1               5

<210> SEQ ID NO 9
<211> LENGTH: 9
<212> TYPE: PRT
<213> ORGANISM: Homo sapiens
<220> FEATURE:
<221> NAME/KEY: MOD_RES
<222> LOCATION: (4)
<223> OTHER INFORMATION: 4Hyp

<400> SEQUENCE: 9

Glu Met Thr Pro Val Asn Pro Gly Gln
 1               5

<210> SEQ ID NO 10
<211> LENGTH: 8
<212> TYPE: PRT
<213> ORGANISM: Homo sapiens
<220> FEATURE:
<221> NAME/KEY: MOD_RES
<222> LOCATION: (7)
<223> OTHER INFORMATION: 4Hyp

<400> SEQUENCE: 10

Glu Met Thr Pro Val Asn Pro Gly
 1               5

<210> SEQ ID NO 11
<211> LENGTH: 9
<212> TYPE: PRT
<213> ORGANISM: Homo sapiens
<220> FEATURE:
<221> NAME/KEY: MOD_RES
<222> LOCATION: (7)
<223> OTHER INFORMATION: 4Hyp
```

-continued

<400> SEQUENCE: 11

Glu Met Thr Pro Val Asn Pro Gly Gln
 1               5